US009492095B2

United States Patent
Hornick

(10) Patent No.: US 9,492,095 B2
(45) Date of Patent: Nov. 15, 2016

(54) HEMODYNAMICS-BASED MONITORING AND EVALUATION OF A RESPIRATORY CONDITION

(75) Inventor: Ofer Hornick, Zur Igal (IL)

(73) Assignee: Neetour Medical Ltd., Granot (IL)

( * ) Notice: Subject to any disclaimer, the term of this patent is extended or adjusted under 35 U.S.C. 154(b) by 1119 days.

(21) Appl. No.: 13/513,020

(22) PCT Filed: Dec. 1, 2010

(86) PCT No.: PCT/IL2010/001010
§ 371 (c)(1),
(2), (4) Date: May 31, 2012

(87) PCT Pub. No.: WO2011/067759
PCT Pub. Date: Jun. 9, 2011

(65) Prior Publication Data
US 2012/0238834 A1   Sep. 20, 2012

Related U.S. Application Data

(60) Provisional application No. 61/265,779, filed on Dec. 2, 2009.

(51) Int. Cl.
*A61B 5/00* (2006.01)
*G06F 19/00* (2011.01)
(Continued)

(52) U.S. Cl.
CPC .......... *A61B 5/02416* (2013.01); *A61B 5/002* (2013.01); *A61B 5/0205* (2013.01);
(Continued)

(58) Field of Classification Search
CPC  A61B 5/002; A61B 5/02416; A61B 5/6801; A61B 5/0295; A61B 5/08; A61B 5/0823–5/0826; A61B 5/72; A61B 5/1455–5/14551; A61B 5/1477; G06F 19/34–19/3493
See application file for complete search history.

(56) References Cited

U.S. PATENT DOCUMENTS 5,285,782 A   2/1994  Prosser
5,355,880 A   10/1994 Thomas
(Continued)

FOREIGN PATENT DOCUMENTS

WO   90/07357 A1   7/1990
WO   00/67636      11/2000
(Continued)

OTHER PUBLICATIONS

Boode, W. P et al; "Cardiac Output Measurement Using a Modified Carbon Dioxide Fick Method: A Validation Study in Ventilated Lambs" Pediatric Research; vol. 61; No. 3 (2007); p. 279-283.*
(Continued)

*Primary Examiner* — William Thomson
*Assistant Examiner* — Marie Archer
(74) *Attorney, Agent, or Firm* — Roach Brown McCarthy & Gruber, P.C.; Kevin D. McCarthy

(57) ABSTRACT

Assessment of a respiratory condition of a subject, by acquiring a temporally varying hemodynamic waveform signal related to blood flow in a tissue; deriving from the hemodynamic waveform signal an evaluation of blood $CO_2$; acquiring at least one more signal; and determining the medical condition based on the blood $CO_2$ and the at least one more signal. A device for performing the assessment may include an implement disposable on the subject's skin and structured to acquire a temporally varying hemodynamic waveform signal and derive from the signal a blood $CO_2$ value or a close approximation thereof; an oximeter disposable on the subject's skin and structured to provide an oxygen saturation value of the blood of the subject or a close approximation thereof; and an apparatus structured to evaluate the medical condition of the subject based on the blood $CO_2$ and oxygen saturation or close approximations thereof.

22 Claims, 8 Drawing Sheets

(51) Int. Cl.
| | |
|---|---|
| *A61B 5/024* | (2006.01) |
| *A61B 5/08* | (2006.01) |
| *A61B 5/1477* | (2006.01) |
| *A61B 5/1455* | (2006.01) |
| *A61B 7/00* | (2006.01) |
| *A61B 5/0205* | (2006.01) |
| *A61B 5/0295* | (2006.01) |
| *A61B 5/145* | (2006.01) |

(52) U.S. Cl.
CPC ........... *A61B5/0295* (2013.01); *A61B 5/0816* (2013.01); *A61B 5/0823* (2013.01); *A61B 5/1477* (2013.01); *A61B 5/14542* (2013.01); *A61B 5/14551* (2013.01); *A61B 5/6801* (2013.01); *A61B 5/6824* (2013.01); *A61B 5/6831* (2013.01); *A61B 5/6833* (2013.01); *A61B 7/003* (2013.01); *G06F 19/34* (2013.01); *A61B 5/7275* (2013.01)

(56) References Cited

U.S. PATENT DOCUMENTS

| | | | |
|---|---|---|---|
| 5,766,127 | A | 6/1998 | Pologe |
| 6,129,675 | A * | 10/2000 | Jay .................. 600/485 |
| 6,501,975 | B2 | 12/2002 | Diab |
| 6,609,016 | B1 * | 8/2003 | Lynn .................. 600/323 |
| 6,741,876 | B1 | 5/2004 | Scecina |
| 6,802,812 | B1 | 10/2004 | Walker |
| 6,819,950 | B2 | 11/2004 | Mills |
| 6,826,419 | B2 | 11/2004 | Diab |
| 6,896,660 | B2 | 5/2005 | Jelliffe |
| 6,942,622 | B1 | 9/2005 | Turcott |
| 7,195,013 | B2 | 3/2007 | Lurie |
| 7,225,013 | B2 | 5/2007 | Geva |
| 7,341,560 | B2 | 3/2008 | Henderson |
| 7,351,203 | B2 | 4/2008 | Jelliffe |
| 7,405,055 | B2 | 7/2008 | Dunn |
| 2002/0062070 | A1 | 5/2002 | Tschupp et al. |
| 2002/0077535 | A1 | 6/2002 | Finarov |
| 2002/0082485 | A1 | 6/2002 | Faithfull |
| 2002/0110849 | A1 | 8/2002 | Leonhardt et al. |
| 2003/0060690 | A1 | 3/2003 | Jelliffe |
| 2004/0102687 | A1 | 5/2004 | Brashears et al. |
| 2004/0133086 | A1 | 7/2004 | Ciurczak |
| 2004/0204638 | A1 | 10/2004 | Diab |
| 2004/0236240 | A1 | 11/2004 | Kraus |
| 2004/0260161 | A1 | 12/2004 | Melker et al. |
| 2005/0076909 | A1 | 4/2005 | Stahmann |
| 2006/0077063 | A1 * | 4/2006 | Cheng et al. .............. 340/573.1 |
| 2007/0027375 | A1 | 2/2007 | Melker |
| 2007/0129645 | A1 | 6/2007 | Hartley |
| 2007/0191697 | A1 * | 8/2007 | Lynn et al. ................... 600/323 |
| 2007/0208235 | A1 | 9/2007 | Besson |
| 2007/0225612 | A1 | 9/2007 | Mace |
| 2008/0076993 | A1 | 3/2008 | Ostrowski |
| 2008/0188733 | A1 | 8/2008 | Al-Ali et al. |
| 2008/0190430 | A1 | 8/2008 | Melker |
| 2009/0257980 | A1 | 10/2009 | Davies |

FOREIGN PATENT DOCUMENTS

| | | |
|---|---|---|
| WO | 02/45566 | 6/2002 |
| WO | 2009/144723 | 12/2009 |

OTHER PUBLICATIONS

Roussos, C. et al "Respiratory Failure"; Eur Respir J 2003; 22: Suppl. 47, 3s-14s.*
Astin W. T; "The relationships between arterial blood oxygen saturation, carbon dioxide tension, and pH and airway resistance during 30 per cent oxygen breathing in patient with Chronic Bronchitis with Airway Obstruction"; American Review of Respiratory Disease, vol. 102 (1970) pp. 382-387.*
Paulev, P-E. et al; "Clinical application of the pO2—pCO2 diagram"; Acta Anaesthesiol Scand 2004; 48: 1105-1114.*
Hughes, J.M. B; "Pulmonary Gas Exchange"; Eur Respir Mon, 2005, 31, 106-126.*
West, J. B. et al"Pulmonary Gas Exchange" Am J Respir Crit Care Med vol. 157. pp. S82-S87, 1998.*
AARC guideline for intrahospital transport of mechanically ventilated patients; Respiratory Care. Jun. 2002 vol. 47 No. 6, 721-723.
AARC Clinical Practice Guideline. Management of Airway Emergencies. Reprinted from the Jul. 1995 issue of Respiratory Care [Respir Care 1995; 40(7): 749-760] .
Akça (2006) Optimizing the intraoperative management of carbon dioxide concentration. Curr Opin Anaesthesiol 19(1): 19-25.
Alemi and Neuhauser (2004) Time-between control charts for monitoring asthma attacks. Jt Comm J Qual Saf 30(2): 95-102.
American Society of Anesthesiologists Task Force on Sedation and Analgesia by Non-Anesthesiologists, Practice guidelines for sedation and analgesia by non-anesthesiologists. Anesthesiology. 2002; 96: 1004-1017.
Barberá et al., (1997) Mechanisms of worsening gas exchange during acute exacerbations of chronic obstructive pulmonary disease. Eur Respir J 10(6): 1285-91.
Becker and Casabianca (2009) Respiratory monitoring: physiological and technical considerations. Anesth Prog 56(1): 14-22.
Belpomme et al., (2005) Correlation of arterial PCO2 and PETCO2 in prehospital controlled ventilation. Am J Emerg Med 23(7): 852-9.
Bouillon et al., (1999) Pharmacokinetic-pharmacodynamic modeling of the respiratory depressant effect of alfentanil. Anesthesiology 91(1): 144-55.
Burge and Wedzicha (2003) COPD exacerbations: definitions and classifications. Eur Respir J Suppl 41: 46s-53s.
Franciosi et al., (2006) Markers of exacerbation severity in chronic obstructive pulmonary disease. Respir Res 7: 74.
Gainnier et al., (2003) Prone position and positive end-expiratory pressure in acute respiratory distress syndrome. Crit Care Med 31(12): 2719-26.
Guthrie et al., (2007) End-tidal carbon dioxide measurements in children with acute asthma. Acad Emerg Med 14(12): 1135-40.
Hinkelbein et al., (2008) Accuracy and precision of three different methods to determined PCO2 (PaCO2 vs. PetCO2 vs. PTcCO2) during interhospital ground transport of critically ill and ventilated adults. J Trauma 65(1): 10-8.
Johnson et al., (1984) Circumstances of death from asthma. Br Med J (Clin Res Ed) 288(6434): 1870-2.
Kerr and Mills (2001) Intra-operative and post-operative hypercapnia leading to delayed respiratory failure associated with transanal endoscopic microsurgery under general anaesthesia. Br J Anaesth 86(4): 586-9.
Mays (1973) An arterial blood gas diagram for clinical use. Chest 63(5): 793-800.
McCrory et al., (2001) Management of acute exacerbations of COPD: a summary and appraisal of published evidence. Chest 119(4): 1190-209.
Moller (2005) Evidence-based Resource in Anaesthesia and Analgesia, 2nd Edn. M. R. Tramer (editor). Published by BMJ books, London. pp. 194; indexed; illustrated. Br J Anaesth 94 (5): 695.
Poulose (2005) CO2 retention in acute severe asthma. Chest 127(5): 1867.
Ray et al., (2006) Acute respiratory failure in the elderly: etiology, emergency diagnosis and prognosis. Crit Care 10(3): R82.
Riphaus et al., (2009) S3 guideline: sedation for gastrointestinal endoscopy 2008. Endoscopy 41: 787-815.
Rodrigo et al., (2004) Acute asthma in adults: a review. Chest 125(3): 1081-102.
Sasse et al., (1996) Arterial blood gas changes during breath-holding from functional residual capacity. Chest 110(4): 958-64.
Seguin et al., (2001) The measurement of end-tidal carbon dioxide (PETCO2) is not a significant parameter to monitor in patients with severe traumatic brain injury. Can J Anesth 48(4): 396-400. Translated abstract.
Yosefy et al., (2004) End tidal carbon dioxide as a predictor of the arterial PCO2 in the emergency department setting. Emerg Med J 21(5): 557-9.

* cited by examiner

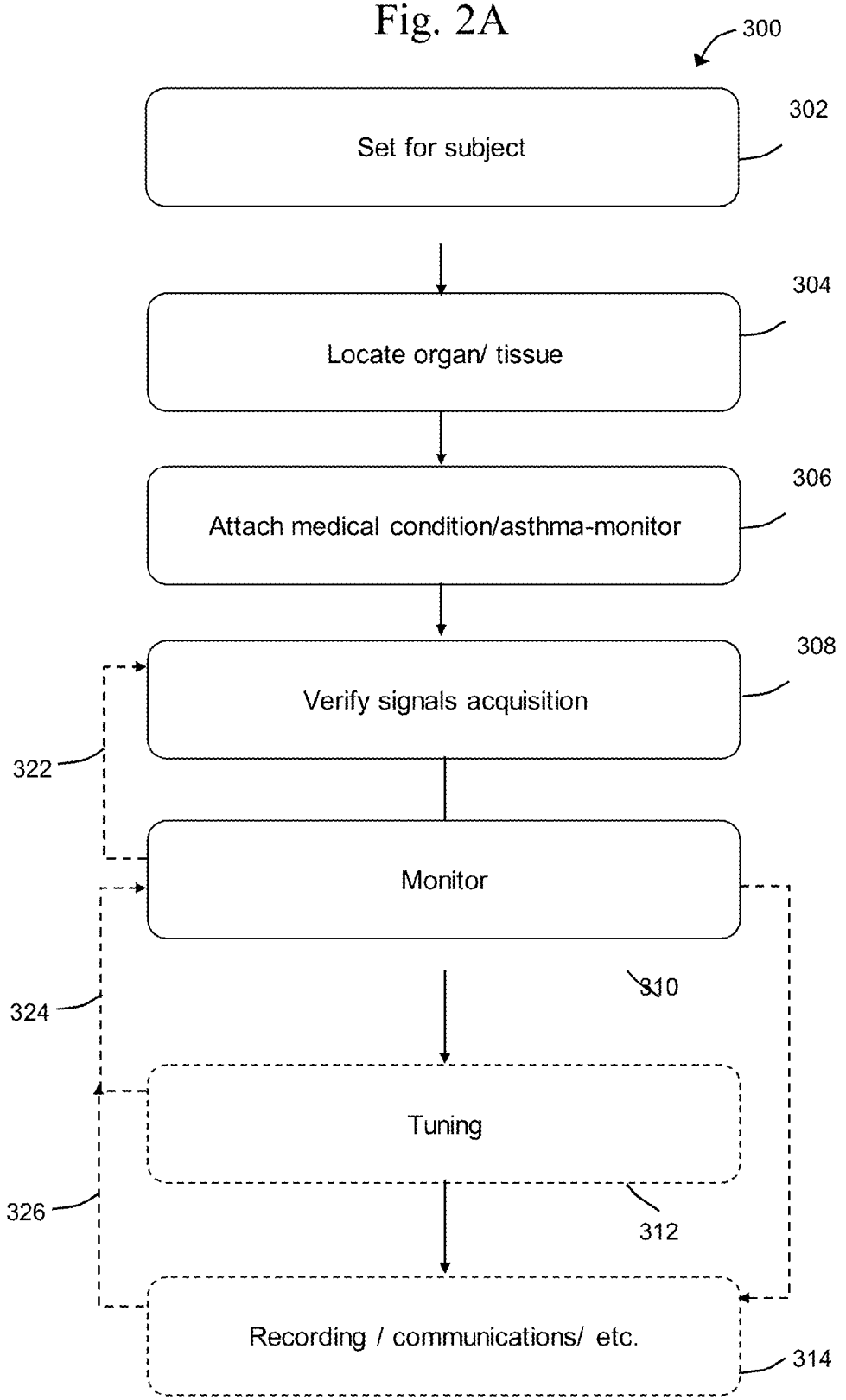

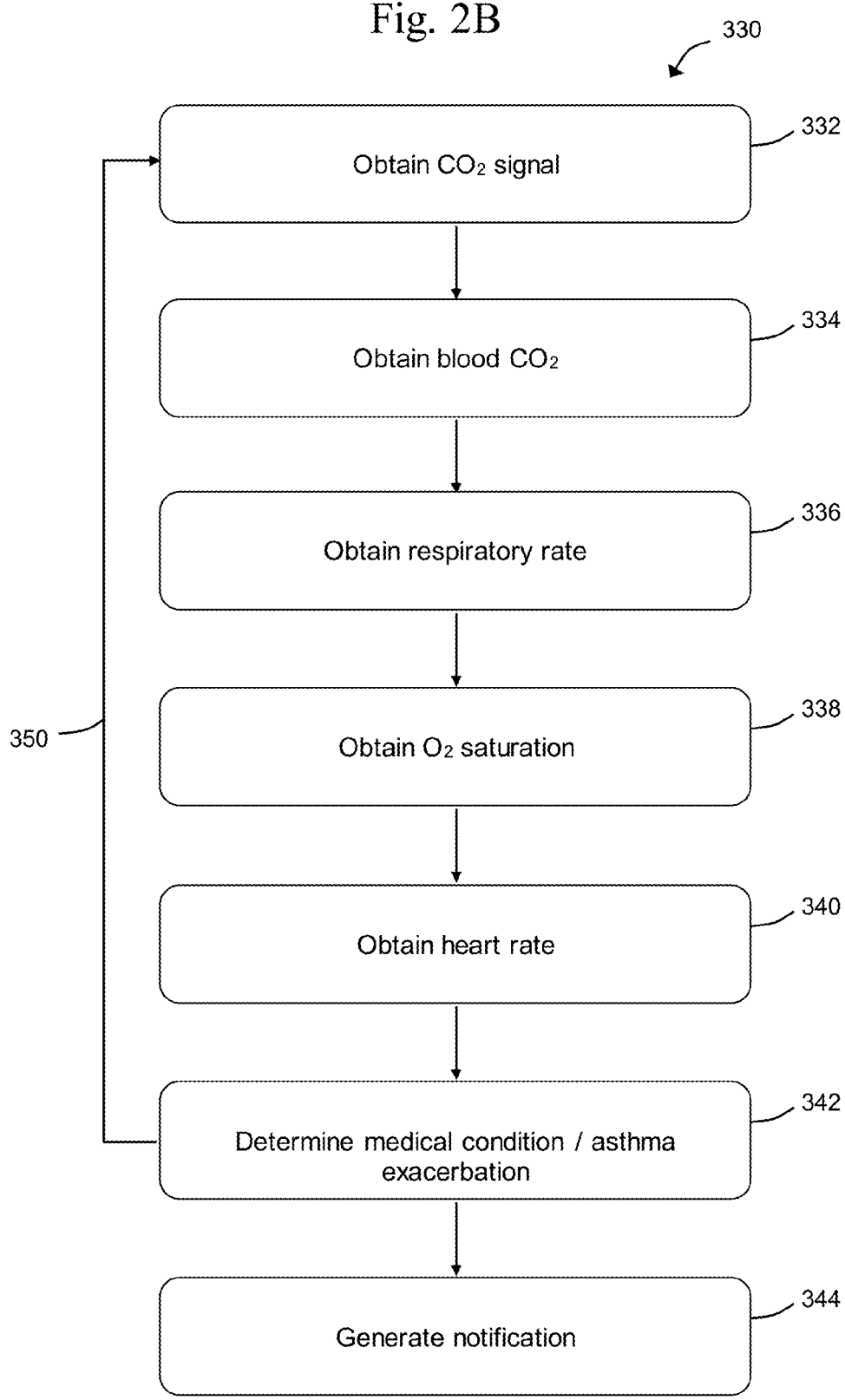

HEMODYNAMICS-BASED MONITORING AND EVALUATION OF A RESPIRATORY CONDITION

REFERENCE TO CO-PENDING APPLICATIONS

Priority is claimed as a 371 of international application number PCT/IL2010/001010, filed on Dec. 1, 2010; which claims priority to U.S. Provisional Patent application Ser. No. 61/265,779, filed on Dec. 2, 2009.

FIELD OF THE INVENTION

The present invention relates to monitoring and evaluation of a medical condition and/or respiratory status of a patient, using hemodynamics-based methods and devices.

BACKGROUND OF THE INVENTION

Without adequate respiratory activity, human life is under threat. Oxygen, $O_2$, enters the blood, and carbon dioxide, $CO_2$, is excreted through the alveoli. Due to lung anatomy, not only the volume of breathed air, but also the rate and depth of breathing have a major effect on alveolar ventilation.

Respiratory failure is often difficult to predict and can become life threatening in a few minutes. Respiratory failure can also build up gradually, frequently the result of a chain of more or less related circumstances. The term "respiratory failure" implies the inability to maintain either the normal delivery of oxygen to tissues or the normal removal of carbon dioxide from the tissues. There are, actually, three processes involved in the respiration: the transfer of oxygen across the alveolus, the transport of oxygen to tissues (by cardiac output), and the removal of carbon dioxide from the blood into the alveolus with subsequent exhalation into the environment. Failure of any step in this process can lead to respiratory failure. The mortality related to acute respiratory failure is significant.

Therefore, continuous monitoring of respiratory activity could be life-saving, since a problem in respiratory activity can identify or predict high-risk situations. Monitoring needs to be continuous for two reasons: first, because the physician wants to detect a problem immediately if it occurs, as there may be only a few minutes to treat it properly before irreversible damage to critical organs has occurred; and second, because it may develop gradually—and the physician wants to be able to detect the trend of an imminent respiratory failure, and intervene to change this trend and provide the patient with optimal respiration and gas exchange.

From a clinical point of view, monitoring respiratory activity should include parameters such as respiratory rate and depth, as well as quantifiable information about the degree of gas exchange actually taking place. The ideal respiratory monitor would provide continuous information about all those variables in a non-obtrusive fashion.

As sufficient breathing is such a critical bodily requirement, the response to insufficient breathing is highly developed in animals and human beings, and usually follows a general pattern. Breathing is controlled, to a large extent, by $CO_2$ levels. When breathing only starts to fail, the sympathetic part of the autonomic nervous system is activated, increasing cardiac rate and cardiac output, as well as respiratory rate and depth. The purpose is to increase ventilation and transport of oxygen to tissues. This will usually cause hyperventilation at start, lowering $CO_2$ levels. When these compensatory mechanisms are not sufficient any more (for example, due to fatigue of respiratory muscles), $CO_2$ levels rise, leading to further increases in respiratory rate and depth (and further increases in sympathetic activity, pulse rate etc.), and $O_2$ levels decline.

Therefore, a pattern of failing respiration is usually demonstrated by the following patho-physiological changes: typical changes in $CO_2$ (a compensatory decrease below normal first, than gradual increase above normal values) and $O_2$ (first, normal values or even high oxygen saturation at the first stages of respiratory deterioration when $O_2$ reserves suffice) followed by continuous decline of $O_2$ levels. When respiratory changes develop and go through more severe stages, so does this pattern evolve with higher $CO_2$ levels, lower $O_2$ levels, higher pulse and respiration rates. This pattern may develop acutely (over minutes or hours), or more slowly and chronically. Respiratory failure per-se is usually defined when $PaO_2$ is lower than 60 mmHg and $PaCO_2$ is greater than 50 mmHg.

Once respiratory failure goes beyond the severe stage, it becomes life threatening. In this stage, critical organs start to fail, with the result that high cardiac rate may drop to bradycardia (low rate), and the high respiratory rate turns into feeble efforts of breathing. $PaO_2$ levels are very low, and $PaCO_2$ levels are very high.

By closely following these changes, physicians are able to monitor the patient's respiratory status, provide treatment, verify that the treatment works and that respiration improves or further deteriorates; and make critical decisions regarding additional measures, such as the need for artificial ventilation or its removal. In Asthma conditions, for example, physicians commonly use the GINA table (FIG. 4.4.1 in GINA Report Global Strategy for Asthma Management and Prevention, updated 2008), for determining the severity of the patient's exacerbation. Similar tables and/or guidelines may be used in other respiratory conditions.

The medical literature contains information on how these parameters may be used in the diagnosis and treatment of various conditions, whenever respiratory failure is suspected or the patient is at high-risk of developing it. The general pattern described above appears whenever respiratory failure develops, with some adaptations for different clinical situations.

The physician will use clinical methods and devices that are appropriate for the clinical situation. When the risk is higher, and when the patient's condition seems to be more critical, the physician will often opt for invasive methods, which are the most accurate, such as taking arterial blood gas samples. These provide accurate measurements of arterial $O_2$ and $CO_2$ levels, which allow for accurate evaluation of the patient's respiratory status (at the cost of being invasive, with potentially serious adverse events). Commercial attempts at developing continuous intra-arterial $CO_2$ measuring devices have produced several devices, which generally did not yet obtain substantial commercial success due to cost, complexity and invasiveness.

Mays (Edward E. Mays, *An Arterial Blood Gas Diagram for Clinical Use*, Chest Vol. 63, No. 5, May, 1973; 793-800) has described how arterial blood gases, mainly $PaO_2$ and $PaCO_2$, change with varying degrees of respiratory insufficiency towards respiratory failure, in several groups of respiratory disease patients and based on values measured in normal physiological conditions. The article suggests a simplified diagram, which could help in identifying the stages of respiratory insufficiency that commonly appear before the onset of respiratory failure. According to Mays, "considerable blood gas tension derangement is present for varying time intervals prior to the onset of respiratory failure due to widely different causes. Typically, the arterial carbon dioxide tension ($PaCO_2$) is often decreased early in the course of illness, probably secondary to reflex hyperventilation. This alveolar hyperventilation may be of sufficient magnitude initially to maintain the arterial oxygen tension ($PaO_2$) within the normal range. Therefore, hypocarbia [low $CO_2$] associated with a normal or marginal $PaO_2$ may be the earliest laboratory manifestation of respiratory insufficiency. As the disease severity progresses, the work of breathing increases, incident to increasing airway resistance in chronic obstructive pulmonary disease and to decreasing compliance and alveolar instability in the adult respiratory distress syndrome. In either event, a progressively deteriorating blood gas pattern becomes evident. During this interval of widely varying duration, the $PaO_2$ continues to fall as the initially low $PaCO_2$ rises to normal and finally beyond, and respiratory failure ensues."

As explained by Mays, the relationship between $PaO_2$ and $PaCO_2$ varies at normal breathing, through different stages of respiratory insufficiency and respiratory failure, and under clinical conditions such as hyper vs. hypo ventilation, as well as ventilation/perfusion (V/Q) inequality or mismatch. Mays shows that the relationship between $PaCO_2$ and $PaO_2$ was greatly altered in the majority of patients studied at room air at rest. Patient blood gas values were usually displaced laterally from the normal regression line. The amount of displacement from the line and the direction of displacement from the normal means were related to the degree of severity of disease.

Mays also discusses the effects of age and altitude on these relationships.

The same article also demonstrates that, although the slope of the $PaCO_2$ vs. $PaO_2$ relationship varies with different lung/respiratory pathologies, it invariably remains an inverse relationship—that is, when $PaO_2$ declines, $PaCO_2$ rises.

These relationships become important in clinical monitoring, as current non-invasive respiratory monitoring technologies lack clinical accuracy when pathology develops. For example, the non-invasive End-Tidal $CO_2$ ($EtCO_2$) values measured by a capnograph, do not accurately represent blood $CO_2$ values when lung pathology develops; and oxygen saturation values are highly inaccurate when blood oxygen levels are low. Therefore, the ability to measure blood $CO_2$ in a non-invasive way can differentiate the changes in respiratory status to the highest accuracy, and complement the data obtained by measurements with capnographs, pulse oximeters, respiratory rate monitors, etc. Also, when it is known that a subject has a specific disease, knowledge of specific patterns of changes in respiratory parameters (as described in the medical literature) can be used in individual respiratory monitoring of this subject, to detect changes from these patterns and correct them in time.

Clinical conditions which can potentially cause respiratory depression may occur in a multitude of clinical scenarios. Some of these are: Operating rooms, post anesthesia, intubated or mechanically ventilated patients, airway emergencies, intensive care units, emergency rooms, elective surgery—procedural sedation (in hospital and community), patients breathing supplemental oxygen, head injury and other trauma, respiratory conditions (such as asthma, COPD and others), emergency medical services, prematurity and more.

In addition to the conditions listed above, which raise the risk for occurrence of respiratory depression, the physician also needs to remember that other disease conditions can also be worsened by respiration which is less than optimal. That is to say, if a healthy person can tolerate long periods of sub-optimal breathing, a patient with a cardiac disease, for example, may severely deteriorate after only several minutes with the same level of non-optimal breathing.

Another group of patients who require special attention is the chronic respiratory disease group. Disease conditions such as Asthma, COPD, Cystic Fibrosis, etc. are included. These conditions typically involve disease exacerbations, which limit a patient's respiration and gas exchange considerably. These patients, either during an exacerbation of their chronic condition, or when suffering from another acute medical condition, need special attention and monitoring of their respiration.

The physician also needs to monitor patients who receive specific treatments, which may lead to respiratory complications or inability to promptly diagnose them. This includes patients who are mechanically ventilated, intubated patients, pain treatment (use of narcotic drugs) and patients receiving supplemental oxygen.

Respiratory failure can be caused by central or obstructive mechanisms (or a combination of both). Sometimes, the respiratory failure can be predicted by studying the trend before the failures occur.

The main methods which are currently available for respiratory monitoring, include: detection of movement, volume and tissue composition (chest movements/volumes); airflow sensing, non-invasive monitoring/estimation of blood gas concentrations (Oximeters—oxygen saturation, Capnographs—end tidal $CO_2$, Transcutaneous $CO_2$). Invasive arterial blood gas sampling is used as needed based on the perceived severity of the patient's condition.

Detection of hypoxemia and hypercapnia provide alarm criteria corresponding to those of respiratory failure. However, they mirror different physiological parameters and they do not necessarily go in parallel. Hypercapnia can often precede hypoxemia.

$CO_2$ sensing can detect respiratory failure that can cause hypercapnia or hypoxemia, but it will not detect the hypoxemia itself, which the pulse oximeter can do.

The pulse oximeter gives early warning of hypoxemia, but hypercapnia by itself does not lead to hypoxemia and cannot be detected by pulse oximetery. As the blood volume constitutes a reasonable oxygen reserve, the response of pulse oximetry to apnea is very slow. When $CO_2$ is measured in expired air (capnography), gas sampling is not free of problems, and the correlation to arterial blood concentration is not ideal.

Transcutaneous $CO_2$ measurements cannot detect respiratory activity breath by breath but provide an estimate of the arterial $CO_2$ concentration. Accuracy is affected by cardiovascular function, peripheral perfusion, local tissue metabolism, age and skin thickness.

PCT Publication No. WO2009/144723, to the inventor of the present invention published after the priority date of the current application discloses a device and methods for measuring CO2 levels non-invasively in a subject (hereinafter the '$CO_2$-Meter'), based on hemodynamic parameters. The teachings of the WO 2009/144723 are incorporated herein in their entirety by reference and relevant portions thereof are as follow:

Shape analysis

In some embodiments, the shapes of the cycles are further analyzed by taking the first temporal derivate of the cycles ('the derivative') (314).

FIG. 5 illustrates the aligned and superimposed first temporal derivatives 502 of normalized heart cycles of a waveform. With respect to magnitude scale 514 the maximal points (peaks) of the derivates are aligned a at virtual time t=0 of time scale 512.

Typically, several zones are discerned in the derivative shape, as listed in Table 1 below (and with respect to FIG. 5 that shows corresponding numerals):

| Numeral label | Zone | Approximate typical time (ms) |
| --- | --- | --- |
| 1 | First maximum point (global maximum) | 0 |
| 2 | First Minimum point | 50 |
| 3 | Second maximum (alternatively as an inflection point) | 80 |
| 4 | Second minimum | 125 |
| 5 | Third maximum point | 150 |
| 6 | Third minimum point | 220 |

Table 1

In some embodiments, before further analysis, the derivates are pre-processed including, without limiting, the following steps:

Rejection (ignoring or discarding) of outliers (316), such as derivative signals that do not fit the expected and/or the general shape of the majority of the cycles. In some embodiments, the rejection is based on median filter of properties of the signals such as area or height or width of the derivatives signals 502 that do not conform to a predefined or determined (e.g. learned from pervious or other measurement) set of constraints. Optionally, in some embodiments, the rejection is based on the values and/or separation in time of the points in derivates 502 as listed in Table 1, such as first maximal (global) maximum (1) or third minimum (6). For example, if the separation is more or less In 30% of the expected separation. Optionally or additionally, the rejection maybe based on other methods of the art. In case of a single representative cycle this instant step is immaterial.

Smoothing the retained (non-rejected) derivates, such as by a low pass filter to remove noise such as due to derivative properties or to remove residual effects of breathing.

The shapes of derivatives 502, or selected typical derivatives shapes, are combined (e.g. average, weighted average, median selection) to form a representative derivative shape (318) (unless a single representative shape was previously obtained and the derivate of which was taken). In order to reduce sensitivity to variations and possible distortions in the signals, in some embodiments derivates 502 are selected within a sinificantly longer time span than a typical respiration cycle (e.g. several respirations cycles such as 30 or 60 seconds) or from several acquisitions.

FIG. 6 illustrates a representative first temporal derivate 602 of normalized heart cycles of a waveform (hereinafter, also 'ShapeD'). The illustration is with respect to relative magnitude scale 614 and time axis scale 612 (similar to time scale 512 of FIG. 5). wherein the maximal value (T in FIG. 5) is taken as 100%. FIG. 6 also illustrates auxiliary lines and features (e.g. 'pi', V) to further clarify the discussion below and reference to FIG. 6 is accordingly implied.

Representative first temporal derivate ShapeD is further analyzed to obtain key points and features in ShapeD) (320) as follows:

Determine the points in ShapeD where the initial (temporal, time-wise) ascent and descent are at 50% of the peak (100%), namely, pi and p2, respectively. Optionally or alternatively, instead of using the 50% level, the inflection point level of the rise or fall, or combination thereof is used (such as by averaging or time-wise distance between the inflection points).

Calculate the time-wise distance between points pi and p2 (hereinafter, 'wid' equivalent to V in FIG. 6).

Determine the tangent 604 to the initial temporal descent at point p2.

Determine the intersection of tangent 604 with the time axis 612 to obtain intersection point p3.

Compute the integral between ShapeD and time axis 612 between intersection point p3 and p3+wid (timewise), shown as striped region 606 and 606a (collectively 606). Since ShapeD is a representative first derivate of the normalized heart cycles, integral 606 is equivalent to the difference between the normalized cycle between corresponding point p3 and p3+wid. A possible rationale behind the above procedure is to calculate a normalized value from a cycle, where this value represents the decay of the heart cycle signal, from the "expected maximum point" represented as point p3.

It was unexpectedly found that the value of integral 606 (hereinafter also 'AreaD') tracks, at least approximately, the $CO_2$ level, (and may be regarded also as haemodynamic parameter or index).

$CO_2$ evaluation derivation

In some embodjments of the invention $CO_2$ level ('$CO_2L$'), at least with an approximate relation to a capnograph, is derived from AreaD (322) as follows. The functional expression for obtaining $CO_2L$ is expressed as:

$$CO_2L = M \times AreaD + N \quad (1)$$

In some embodiments, a sufficiently (such as of clinical significance) approximation is achieved by setting coefficient 'M' as M=80. Optionally, other values are used, optionally or additionally, by determining or adjusting coefficient 'M' according to previous measurements or other references such as blood samples.

In some embodiments, coefficient 'N' can be derived by calibration of $CO_2L$ relative to a reference such as a capnograph or according to blood samples or intraarterial $CO_2$ analyzer. Optionally or alternatively, $CO_2L$ is calibrated assuming a normal physiology and/or condition of the patient which can be monitored and assessed according to the signals (such as 502 of FIG. 5). Normal physiology and/or condition, which may also be obtained by using the same detection apparatus or an auxiliary detection apparatus, are, for example, normal breathing (e.g. about 6 seconds per cycle), normal heart rate (e.g. about 60-70 bps) or normal $SpO_2$, or combinations thereof. Assuming $CO_2L$ in normal conditions to be about 38mmHg, coefficient 'N' is obtained from formula (1) by:

$$N = CO_2L - M \times AreaD \quad (2)$$

In some embodiments of the invention, coefficient 'N' is adjusted or determined periodically or responsive to perceived (detected) change of the patient condition, and some previously determined values of $CO_2L$ may be used as in formula (2) above. In some embodiments of the invention, one or more of the coefficients 'M' and 'N' may he obtained by comparing and/or correlating the detected signal (such as waveform 102) to a typical or representative corresponding detected signal, or by comparing and/or correlating ShapeD to a typical or representative derivative of $CO_2$ signal in a normal or typical patient. See also discussion on using templates and limits below.

In some embodiments of the invention, a better accuracy of and/or sensitivity to $CO_2$ levels are achieved by non-linear formulas or other methods (eg. fuzzy logic) and the parameters of the formulas (e.g. polynomial or exponent) or settings of the methods are calibrated and adjusted similarly as described for formulas (1)-(2). The non-linear computation is, in some embodiments, beneficial relative to the linear computations in cases of seemingly non-realistic high and/or low $CO_2$ levels that were derived linearly such as by formulas (1)-(2) above.

Wherein the referred figures, namely FIG. 5 and FIG. 6, are as disclosed in WO2009144723.

Therefore, the need for reliable and convenient respiratory monitoring is well known to the clinical community. The clinician generally requires several different variables, such as respiratory rate, tidal volume, apnea events and blood gas concentration. Ideally, it should be possible to obtain these without disturbing or harming the patients.

SUMMARY OF THE INVENTION

The present invention relates to assessment or evaluation of a medical condition and/or a respiratory status of a subject based on blood $CO_2$ estimation acquired using non-invasive apparatus and/or methods, providing an accurate assessment of a subject's respiratory status.

In some embodiments, the device and methods of PCT Publication No. WO2009/144723, and variations thereof (hereinafter also designated the '$CO_2$-Meter'), are used, modified and/or augmented to acquire additional signals such as $O_2$ level (e.g. saturation), respiratory rate, airflow rate, heart rate or wheeze sound, or close approximations thereof, and use the additional one or more signals to evaluate or assess the respiratory status in medical conditions in which respiratory status is important or in which the risk of respiratory failure is high. In some embodiments, the additional signals are also acquired non-invasively.

In some embodiments, the respiratory status condition is evaluated according to accepted or recommended medical guidelines.

As will be explained below, the ability to measure $CO_2$ in blood is said to provide the best measure of ventilation; and thus, the ability to non-invasively measure $CO_2$ in blood, as done by the $CO_2$-Meter, provides a new method to assess respiratory status with a level of accuracy that was previously done, usually, by use of invasive methods such as arterial blood gas sampling. The $CO_2$ value is of clinical value by itself; and when additional parameters are simultaneously evaluated, the respiratory status can be evaluated with even higher accuracy.

In some embodiments, the device can be manually adjusted to adapt to age groups of subjects (e.g. infants, children or elderly subjects), and optionally to the clinical situation of the subject (e.g. after trauma or medical history). Optionally or additionally, the device may be adjusted to adapt according to the behavior or symptoms of a particular subject during respiratory monitoring in order to avoid missing risky conditions and/or to avoid false alarms.

In some embodiments, under certain respiratory or other clinical conditions or circumstances, the device can be manually set to relate occurring situations to particular indications, and based on such settings the device may optionally adjust working parameters thereof for future operations. The device can store in memory thereof, or send to other resources, events that occurred during the operation, such as determination of disease exacerbations, corresponding working parameters, or change of settings or any value that might be helpful for future analysis of the subject ongoing conditions and/or the device operation ('recording', 'trending').

In some embodiments, based on past results and/or trending the device may adjust to varying situations ('learning').

In some embodiments, the device is equipped with communication apparatus providing telemedicine capabilities and other remote operations.

In typical embodiments the apparatus is a battery operated portable device that can be worn on the subject, such as on or around an arm. The device provides indications as to the assessment or evaluation of respiratory condition of the subject such as audible and/or graphical and/or color and/or alphanumeric notifications, as well as other alerts such as vibrations. In some preferred embodiments the device is suitable for personal use at home or on travel as well as for ambulatory and first aid use.

In the specification and claims the following terms and derivatives and inflections thereof imply the respective non-limiting characterizations below, unless otherwise specified or evident from the context.

$CO_2$, $O_2$—denote carbon dioxide and molecular oxygen, respectively.

$PaCO_2$—$CO_2$ partial pressure in the blood or an approximation thereof sufficiently close to indicate a clinical state or a physiological state of a subject.

$CO_2$ (or $O_2$) level—a value representing or reflecting a concentration of the gas, such as partial pressure in exhaled air or blood.

Subject—a person monitored for a medical condition, in some cases including a guardian thereof such as a parent of a child.

Hemodynamic (signal, parameter)—a temporal signal having a varying waveform with respect to time and relating to blood flow or resistance in a blood vessel or vessels of an organ or tissue or part thereof.

Assessment (of a value or a condition)—derivation of a value or a close approximation thereof based on other values and/or circumstances and/or conditions. Assessment, evaluation and determination are used herein synonymously unless clearly evident otherwise.

Assessment (of medical condition/exacerbation)—derivation of a medical condition or a close approximation thereof based on symptoms of the subject and/or signals acquired from a subject.

Real-time—a sufficiently rapid operation or response as required by an intended use of an apparatus or necessitated by a process or phenomenon being observed.

Monitoring—continuous real-time evaluation, optionally periodic with intermediate delays, without precluding one-time or irregularly recurring evaluations.

As referred herein a signal is not necessarily a raw (directly acquired) signal but in some embodiments, without limiting, represents a processed signal or a value derived from an acquired signal. A signal or a derivation thereof denotes or indicates a measure or data of a subject, or an approximation thereof sufficiently close to indicate a clinical state or a physiological state of a subject (close approximation).

There is therefore provided, in accordance with an embodiment a method for assessment of a respiratory condition of a subject, the method comprising: acquiring from the subject a temporally varying hemodynamic waveform signal related to blood flow in a tissue of the subject;

deriving from the hemodynamic waveform signal an evaluation of blood carbon dioxide ($CO_2$) of the subject; acquiring from the subject at least one more signal related to the respiratory status or cardiovascular status of the subject; and determining the respiratory condition of the subject based on the blood $CO_2$ and the at least one more signal.

There is further provided, in accordance with an embodiment, a device for evaluating a respiratory condition of a subject, the device comprising: an implement disposable on the subject's skin and structured to acquire a temporally varying hemodynamic waveform signal and derive from the signal a blood $CO_2$ value of the subject or a close approximation thereof; an oximeter disposable on the subject's skin and structured to provide an oxygen saturation value of the blood of the subject or a close approximation thereof; and an apparatus structured to evaluate the respiratory condition of the subject based on the blood $CO_2$ and oxygen saturation of the blood of the subject or close approximations thereof.

In some embodiments, the hemodynamic waveform signal is acquired during an exacerbation of an existing, previously known condition of the subject.

In some embodiments, the existing, previously known condition of the subject comprises one or more of asthma, Chronic Obstructive Pulmonary Disease (COPD), cystic fibrosis, a chronic respiratory disease, metabolic derangement, a chronic cardiac condition and head trauma.

In some embodiments, the existing, previously known condition of the subject comprises one or more of mechanical ventilation of the subject, supplemental oxygen intake by the subject, and medication use by the subject.

In some embodiments, the medical condition comprises an asthma exacerbation.

In some embodiments, determining the asthma is according to recommended guidelines.

In some embodiments, the recommended guidelines comprises at least one of Global Initiative for Asthma (GINA) and National Institutes of Health (NIH).

In some embodiments, the hemodynamic waveform signal is acquired non-invasively.

In some embodiments, the at least one more signal is acquired non-invasively.

In some embodiments, the at least one more signal comprises at least one of a respiratory rate, a heart rate, airflow rate, oxygen saturation, a wheeze sound or a close approximation thereof.

In some embodiments, the at least one more signal comprises at least respective close approximations of at least one of a respiratory rate, a heart rate and oxygen saturation.

In some embodiments, the respiratory rate is derived from the hemodynamic waveform signal.

In some embodiments, the method further comprises notifying the determined medical condition.

In some embodiments, notifying the medical condition comprises providing at least one of an alphanumeric display, a graphical display, a color display, audio alerts, voice alerts or vibration or any combination thereof.

In some embodiments, the device further comprises equipment providing one or more additional signals of the subject, or a close approximation thereof, and wherein the apparatus is further structured to evaluate the medical condition of the subject based also on the one or more additional signals.

In some embodiments, the apparatus is structured to evaluate the respiratory condition of the subject based on the blood $CO_2$ and oxygen saturation of the blood of the subject or close approximations thereof, and at least one of a provided respiration rate, heart rate, wheeze sound, pulsus paradoxus, or close approximations thereof.

In some embodiments, the apparatus is structured to provide the respiration rate of the subject, or a close approximation thereof, from the temporally varying hemodynamic waveform signal.

In some embodiments, the oximeter is structured to provide the heart rate of the subject, or a close approximation thereof.

In some embodiments, the apparatus is structured to provide the heart rate of the subject, or a close approximation thereof, from a photoplethysmography (PPG) signal provided by the oximeter.

In some embodiments, the apparatus is structured to provide the heart rate of the subject, or a close approximation thereof, from the hemodynamic waveform signal.

In some embodiments, the device further comprises equipment to provide at least one of a respiration rate or heart rate of the subject, or close approximations thereof.

In some embodiments, the device further comprises equipment to provide a representation of wheeze sound of the subject, or a close approximation thereof.

In some embodiments, the device further comprises equipment to provide a representation of pulsus paradoxus of the subject, or a close approximation thereof.

In some embodiments, the apparatus is structured to evaluate the medical condition of the subject according to provided guidelines.

In some embodiments, the device comprises notification equipment for notifying the respiratory condition, and the apparatus is structured to provide a notification according to the respiratory condition.

In some embodiments, the device is structured to provide evaluation of the respiratory condition in real-time.

In some embodiments, the device is structured to provide continuous real time evaluation of the respiratory condition.

In some embodiments, the apparatus comprises at least one processor and a memory operatively coupled to the at least one processor, a portion of the memory having a processor readable and executable program embodied therein coded to evaluate the respiratory condition of the subject.

In some embodiments, the apparatus is sufficiently small for mobile use.

In some embodiments, the apparatus is sufficiently small and lightweight for wearing by the subject.

In some embodiments, the apparatus is sufficiently mobile to be worn by an ambulatory subject.

In some embodiments, the apparatus further comprises a user interface enabling manual input of symptomatic information, to be used by the apparatus structured for enhancing the evaluation of the medical condition.

In addition to the exemplary aspects and embodiments described above, further aspects and embodiments will become apparent by reference to the figures and by study of the following detailed description. The following embodiments and aspects thereof are described and illustrated in conjunction with systems, tools and methods which are meant to be exemplary and illustrative, not limiting in scope.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 2A illustrates a flowchart concisely outlining actions for assessment of disease exacerbations, according to exemplary embodiments of the invention;

FIG. 2B illustrates a flowchart outlining actions during monitoring of assessment of disease exacerbations, according to exemplary embodiments of the invention;

DETAILED DESCRIPTION

Figure 1:
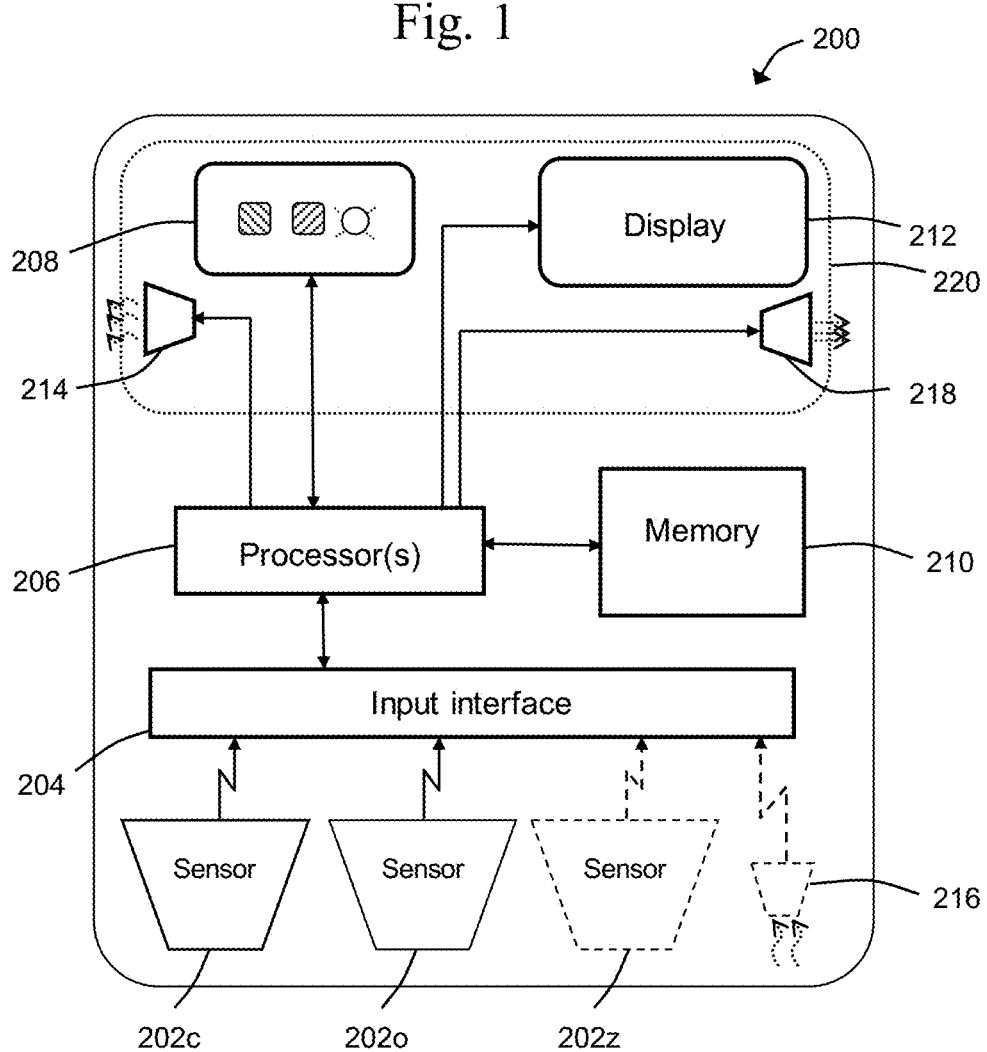
FIG. 1 schematically illustrates a block diagram of a monitor for respiratory monitoring/respiratory disease exacerbations, according to exemplary embodiments of the invention.

The present invention provides devices and methods for assessment of a medical condition of a subject, by acquiring from the subject a temporally varying hemodynamic waveform signal related to blood flow in a tissue of the subject; deriving from the hemodynamic waveform signal an evaluation of blood $CO_2$ of the subject; acquiring from the subject at least one more signal; and determining the medical condition of the subject based on the blood $CO_2$ and the at least one more signal. A device for performing the assessment may include an implement disposable on the subject's skin and structured to acquire a temporally varying hemodynamic waveform signal and derive from the signal a blood $CO_2$ value of the subject or a close approximation thereof; an oximeter disposable on the subject's skin and structured to provide an oxygen saturation value of the blood of the subject or a close approximation thereof; and an apparatus structured to evaluate the medical condition of the subject based on the blood $CO_2$ and oxygen saturation of the blood of the subject or close approximations thereof.

The following description relates to one or more non-limiting examples of embodiments of the invention. The invention is not limited by the described embodiments or drawings, and may be practiced in various manners or configurations or variations. The terminology used herein should not be understood as limiting unless otherwise specified.

The non-limiting section headings used herein are intended for convenience only and should not be construed as limiting the scope of the invention.

General Terminology

The terms 'about', 'close', 'approximate' and 'practically' denote a respective relation or measure or amount or quantity or degree that has no adverse consequence or effect relative to the referenced term or embodiment or operation or the scope of the invention.

The terms 'preferred', 'preferably', 'typical', 'typically' or 'optionally' do not limit the scope of the invention or embodiments thereof.

The term 'may' denotes an option which is either or not included and/or used and/or implemented, yet the option constitutes at least a part of some embodiments of the invention without limiting the scope thereof.

The terms 'comprises', 'comprising', 'includes', 'including', 'having' and their inflections and conjugates denote 'including but not limited to'.

Unless the context indicates otherwise, referring to an object in the singular form (e.g. "a thing" or "the thing") does not preclude the plural form (e.g. "the things").

The terms 'processor' or 'computer' (or system thereof) is used herein as ordinary context of the art, typically comprising additional elements such as memory or communication ports. Optionally or additionally, terms 'processor' or 'computer' or derivatives thereof denote an apparatus that is capable of carrying out a provided or an incorporated program and/or is capable to controlling and/or accessing data storage apparatus and/or other apparatus such as input and output ports (e.g. general purpose micro-processor, RISC processor, DSP). The terms 'processor' or 'computer' denote also a plurality of processors or computers connected, and/or linked and/or otherwise communicating, possibly sharing one or more other resources such as memory.

The terms 'software', 'program', 'software procedure' ('procedure') or 'software code' ('code') may be used interchangeably, and denote one or more instructions or directives or circuitry for performing a sequence of operations that generally represent an algorithm and/or other process or method. The program is stored in or on a medium (e.g. RAM, ROM, disk, etc.) accessible and executable by an apparatus such as a processor or other circuitry.

The processor and program may constitute the same apparatus, at least partially, such as an array of electronic gates (e.g. FPGA, ASIC) designed to perform a programmed sequence of operations, optionally comprising or linked with a processor or other circuitry.

Overview

A general non-limiting overview of practicing the invention is presented below. The overview outlines exemplary practice of embodiments of the invention, providing a constructive basis for variant and/or alternative and/or divergent embodiments, some of which are subsequently described.

As an exemplary guideline, reference is made to GINA (FIG. 4.4.1 in GINA Report Global Strategy for Asthma Management and Prevention, updated 2008), and to Table-1 below which lists vital parameters in the development of respiratory insufficiency towards respiratory failure, which was composed by the inventor, in part based on GINA.

TABLE 1

| | | Status: | | | | |
|---|---|---|---|---|---|---|
| | Grade: | Normal<br>0 | Mild<br>1 | Moderate<br>2 | Severe<br>3 | Critical<br>4 |
| Respiratory rate<br>(breaths/min) | | Normal<br>(10-14) | Increased | Increased | Often ><br>30/min | Weak,<br>unstable |

TABLE 1-continued

| Grade: | Status: | | | | |
|---|---|---|---|---|---|
| | Normal 0 | Mild 1 | Moderate 2 | Severe 3 | Critical 4 |
| Heart rate (pulse/min) | Normal (60-100) | <100 | 100-120 | >120 | <60 |
| $PaCO_2$ | Normal (36-44) | <45 mmHg (typ. 30-35) | <45 mmHg (typ. 36-38) | Normal - pseudo (typ. 39-44) | >45 mmHg possible respiratory failure | >50 mmHg |
| $SpO_2$% | Normal (>95%) | >95% | 91-95% | <90% | <<90% |

In Table-1 the asthma exacerbations (or status thereof) are coded or mapped into grades, where normal is coded as grade 0, mild as 1, moderate as 2, severe as 3 and imminent respiratory arrest (critical) as grade 4.

As an example an adult subject is monitored for $PaCO_2$, $SpO_2$, respiratory rate and heart rate as exemplary signals.

Assuming the values are obtained as shown in Table-2 below.

TABLE 2

| Signal | Value | Unit | Grade |
|---|---|---|---|
| Heart rate | 130 | PPM | 3 |
| Respiratory rate | 35 | BPM | 3 |
| $SpO_2$ | 89 | % | 3 |
| $PaCO_2$ | 47 | mmHg | 3 |

The grades are averaged providing a combined grade of 3 (severe respiratory insufficiency).

As another example, assuming the values are obtained as shown in Table-3 below, where $PaCO_2$ is 40 which is typically normal.

TABLE 3

| Signal | Value | Unit | Grade |
|---|---|---|---|
| Heart rate | 130 | PPM | 3 |
| Respiratory rate | 35 | BPM | 3 |
| $SpO_2$ | 89 | % | 3 |
| $PaCO_2$ | 40 | mmHg | 0 |

Averaging the grades the combined grade is 2.25, indicating an approximate moderate respiratory insufficiency.

However, considering the other signals a seemingly normal value of $PaCO_2$ may be misleading. Thus, as the other signals are of a quite high grade (severe respiratory insufficiency) the $PaCO_2$ value is considered as a pseudo-normal value (e.g. changing from low to high values when respiratory muscles are starting to fatigue) and assigned the respective severe grade, namely a grade of 3, as in Table-4 below. When this combination of results is measured within a trend of first low $CO_2$, and then normal $CO_2$ with the other parameters abnormal, the probability of a pseudo-normal $CO_2$ value (deteriorating condition) is even higher.

TABLE 4

| Signal | Value | Unit | Grade |
|---|---|---|---|
| Heart rate | 130 | PPM | 3 |
| Respiratory rate | 35 | BPM | 3 |

TABLE 4-continued

| Signal | Value | Unit | Grade |
|---|---|---|---|
| $SpO_2$ | 89 | % | 3 |
| $PaCO_2$ | 40 | mmHg | 3 |

In such a case the combined grade is 3 indicating an approximate severe respiratory insufficiency.

In some embodiments, a signal may be considered more significant than others. For example, according to the clinical condition and history of the subject, such as having had respiration arrests, the $PaCO_2$ is assigned a weight of 2, and the values of Table-4 are given now as in Table-5 below.

TABLE 5

| Signal | Value | Unit | Grade |
|---|---|---|---|
| Heart rate | 130 | PPM | 3 |
| Respiratory rate | 35 | BPM | 3 |
| $SpO_2$ | 89 | % | 3 |
| $PaCO_2$ | 40 | mmHg | 3 × 2 |

The combined grade is now 3.75 indicating a worsening severe condition that may result in respiratory arrest.

A signal weight or significance may also depend on a recent trend or history. For example, in case a recent trend of 2 hours sampling rate provides successive $PaCO_2$ values of 30, 30, 35, 40 (in mmHg, continuously rising), and corresponding respiratory rates are 25, 25, 25, 25 (in BPH, continuously high) and the corresponding $SpO_2$ values are 98, 98, 95, 93 (in percent, continuously declining), then the $PaCO_2$ weight is increased (e.g. doubled) or assigned a value depending on the other signals (e.g. one above the average thereof).

In some embodiments, the grade assigned to a signal depends on the value with respect to range thereabout. For example, referring to Table-2 above, $SpO_2$ is 89 which is considered as a severe condition, yet it is just slightly below a moderate condition value. Thus, taking the range 90-95 to correspond to the range of grades 2-3 (or any other plausible correspondence), the value of 89 results in grade 3.20, and Table-2 will be modified accordingly to Table-6 below.

TABLE 6

| Signal | Value | Unit | Grade |
|---|---|---|---|
| Heart rate | 130 | PPM | 3 |
| Respiratory rate | 35 | BPM | 3 |
| $SpO_2$ | 89 | % | 3.2 |
| $PaCO_2$ | 47 | mmHg | 3 |

The combined grade is now 3.05 indicating a severe respiratory insufficiency.

Edward E. Mays, *An Arterial Blood Gas Diagram for Clinical Use*, Chest, Vol. 63, No. 5, May, 1973; 793-800 provides a diagram illustrating the relationships between $PaCO_2$ and $PaO_2$, and how these values change with varying degrees of respiratory insufficiency towards respiratory failure.

Per Mays, to use the diagram, the user should plot patient value (resting, exercising or hyperventilating) on appropriate intercept. Values which indicate V/Q disturbance are quantitated by reference to the slanting isopleths to left of, and paralleling, the normal regression slope. Degree of V/Q disturbance is expressed in millimeters of mercury predicted-observed $PaO_2$ difference, at the level of alveolar ventilation reflected by the observed $PaCO_2$. Normal and failure zones are self-explanatory.

In the individual patient, the data obtained from measurement of the vital parameters described above (such as $PaCO_2$ and $SpO_2$) could be interpreted against a programmed table based on the diagram by Mays, or similar clinically accepted diagrams, to obtain an accurate evaluation of a patient's respiratory status. In some embodiments, data could also be interpreted against a first calibration of accurate patient data, such as arterial blood gas sampling obtained against measurements with the new device.

Signal Acquisition

In some embodiments of the invention, the $CO_2$-Meter is used to obtain $PaCO_2$ or close approximation thereof. Typically, the $CO_2$-Meter is non-invasively attached to the skin and acquires the $CO_2$ hemodynamic waveform signal via a light source and corresponding detector (or sensor).

In some embodiments, respiratory rate is obtained by analyzing the peaks and valleys in the hemodynamic waveform detected by the $CO_2$-Meter and counting the peaks per minute possibly after some averaging or other processing. Optionally or alternatively, the respiratory rate is obtained by other devices and methods such as a belt with sensors that senses the thorax motions or by a nasal sensor that senses temperature variations in the inhaled and exhaled air, changes in air flow, and/or changes in air pressure.

In some embodiments, $SpO_2$ is obtained from a pulse oximeter typically worn on a finger or other location on the skin of the subject.

In some embodiments, the heart rate is obtained by analyzing the hemodynamic waveform detected by the $CO_2$-Meter, or by the $O_2$ saturation signal for peaks and valleys. Optionally or alternatively, other methods may be used such as an ECG monitor or a motion sensor on the skin of the subject to detect pulses in a blood vessel, or any other method known in the art, preferably small and wearable on a subject.

In some embodiments, the $CO_2$-Meter is integrated or coupled with the pulse oximeter, preferably in the same enclosure and optionally sharing a light detector (or sensor or both).

When practical, other signals may also be acquired non-invasively by lightweight preferably wearable apparatus. For example, wheeze may be detected and assessed by mounting a microphone and audio processing apparatus that analyzes wheeze characteristic frequencies in terms of amplitude, rate and relation to respiratory cycles.

Respiratory Monitor Device

The $CO_2$-Meter, or a variation thereof, may be used alone or integrated with other apparatus to form a monitor device for respiratory conditions (hereinafter also 'respiratory-monitor').

In some embodiments, the respiratory-monitor comprises a $CO_2$-Meter and a pulse oximeter, or any elements or parts thereof, such as light photoplethysmography (PPG) probe or probes. Optionally, the respiratory-monitor comprises or is coupled or linked with a microphone for wheeze detection and corresponding voice or audio processor or analyzer.

In some embodiments, the respiratory-monitor comprises a memory or storage device or devices (memory) and at least one processor coupled to the memory or part thereof. A memory portion, preferably a non-volatile memory, is coded with or comprises or embodies a program or part thereof readable and executable by the one or more processors to control the apparatus of the respiratory-monitor and carry out the monitoring and evaluation of the respiratory conditions and any function of the respiratory-monitor.

In some embodiments, the at least one processor comprises one or more of a DSP or an ASIC or any customized or special purpose or general purpose processor. Optionally the respiratory-monitor comprises analog to digital converter to adapt analog signals for digital processing.

In some embodiments, a memory portion is allocated for variables and/or constants that participate in the respiratory-monitoring (work parameters or parameters). Optionally, a memory portion is allocated for recording past values such as past events, past evaluations or past signals (trending).

In some embodiments of the invention, the respiratory-monitor is, preferably, an integrated portable unit sufficiently small and lightweight to be worn on a subject, such as on the wrist or arm, or on a belt, or as part of clothes or on a forehead strap, even by children. In some embodiments, the sensors are attached to fingers or to other body sites where they are possibly hidden under clothing. Preferably the respiratory-monitor is self powered such as by a battery or by a hand-driven generator that loads a capacitor, a rechargeable battery and/or the like.

In some embodiments, the respiratory-monitor comprises user interface for manual inputs or settings, for example, buttons or touch screen or any other mechanism such as dials. In some embodiments, the respiratory-monitor comprises user interface for respiratory indications and/or alerts or any other data, for example, audio sounds, voice alerts, alphanumerical display, graphical or any other displays such as color and/or grayscale coded alerts or charts relatively depicting the exacerbation or any other interaction such as vibrations.

Preferably the respiratory-monitor is sufficiently small for stationary or home or mobile use such as in ambulances, and preferably lightweight to be wearable for home or outside use, such as on travel.

FIG. 1 schematically illustrates a block diagram of a respiratory-monitor (or system) 200, illustrating with arrows the main control linkages between components thereof, according to exemplary embodiments of the invention.

Respiratory-monitor 200 comprises or is connected to sensors (or probes) 202c and 202o for acquiring $CO_2$ and $O_2$ signals, such as $PaCO_2$ and $SpO_2$, respectively, or close approximations thereof. Optionally, system 200 comprises or is connected to additional sensor or sensors represented as 202z and marked with dashed outline, for example, heart rate or respiratory rate sensor or other sensors such as a moisture sensor to assess the agitation state of a subject (see for example GINA and Table-1). Typically and preferably, sensors 202 are attached on or approximate to the skin of the monitored subject (non-invasive detection). In some embodiments, at least sensors 202c and 202o comprise or are implemented as or constitute photoplethysmography probes, and optionally sensors 202c and 202o are integrated or constructed as a combined probe.

It should be noted that $CO_2$ or $O_2$ sensors, 202c and 202o respectively, are used to acquire signals related to $CO_2$ and $O_2$ but are not necessarily particularly sensitive to $CO_2$ or $O_2$, and are denoted as such herein for clarity. For example, in some cases the same apparatus such as light source and radiation detector can be used for both $CO_2$ and $O_2$ (and possibly other constituents) where the difference is in the circuitry or program employed to process the acquired signals.

In some embodiments, system 200 comprises a microphone 216, or alternatively a sensor for sound vibrations (hereinafter 'microphone') to sense wheeze sounds and/or optionally to sense heart rate.

The system operation is carried out by a processor (or processors) 206 according to a program or programs and data stored in memory 210. The program operation is controlled or regulated by user input elements 208 of user interface 220, such as buttons or dials interface or data entered therethrough. The assessed respiratory conditions are indicated on display 212 of user interface 220, along with other data such as feedback to elements 208. Optionally, input elements 208 and display 212 are combined, such as a touch-screen. In some embodiments, display 212 comprises other visual elements such as one or more LED lights.

Memory 210 typically comprises read-only memory and/or read/write memory, optionally comprising portions of non-volatile memory. The output of sensor 202 and microphone 216 is obtained (acquired) via input ports of processor 206 (or other ports) into an interface or buffer 204 for storing the raw data that is further processed. Optionally, interface 204, or part thereof, is comprised in memory 210 or in a module of processor 206, and buffer or interface 204 represents any apparatus for interfacing between a peripheral device (or sensor) and memory 210 and/or processor 206, such as Analog-to-Digital converter (ADC) that is optionally multiplexed between a plurality of sensors 202.

In some embodiments, respiratory-monitor 200 is powered by a power supply connected to mains socket. Preferably, respiratory-monitor 200 is a portable device powered by a battery.

In some embodiments, respiratory-monitor 200 comprises a buzzer 214 representing also any sound indication and/or alarm equipment or mechanism, and in some embodiments system 200 comprises a vibrator 218 representing any equipment or mechanism for tactile indication and/or alarm. In some embodiments, buzzer 214 or vibrator are adapted (or set or tuned) to awake the subject or guardian thereof.

In some embodiments, respiratory-monitor 200 comprises communication apparatus to connect to an auxiliary device with notification and/or human or user interface such as 220 or part thereof for use by another person such as guardian of the subject.

In some embodiments, respiratory-monitor 200 is equipped with or comprises apparatus to enable uploading data from respiratory-monitor 200 (e.g. stored records, see also below) or to enable downloading of data and/or programs such as to upgrade or adapt respiratory-monitor 200 to different subjects.

In some embodiments, respiratory-monitor 200 is equipped with apparatus for telemedicine, for example, enabling a remote physician to assess the condition of the subject and/or offer a treatment.

Operation Overview

FIG. 2A illustrates a flowchart 300 concisely outlining actions for assessment of respiratory exacerbations, according to exemplary embodiments of the invention. In the following discussion reference to respiratory-monitor 200 of FIG. 1 is implied as a non-limiting example.

Typically respiratory symptoms (and normal ranges of physiological parameters) vary between age groups (see for example, GINA and Table-1 for respiratory rate). Accordingly, by using user interface 220 respiratory-monitor 200 is set for the subject age (302). For example, by setting the age the program is directed to use a set of parameters respective to the age for assessing the respiratory condition. In some embodiments, the medical history or clinical state of the subject are considered and in addition to age representative states are selected by user interface 220. Optionally or alternatively, working parameters of the program are modified by user interface 220 to reflect the subject state.

In some embodiments, user interface 220 enables manual input of symptomatic information, to be used by the apparatus structured for enhancing the evaluation of the medical condition. The symptomatic information is based on medical guidelines. For example, see GINA table—such symptomatic information could be the level of activity which causes breathlessness, or the level of alertness, etc; and could be different between different disease conditions.

A suitable organ or tissue for placing respiratory-monitor 200 is located on the subject to be monitored so that sensors 202 would acquire sufficient signals in terms such as amplitude and/or signal to noise ratio (304). The skin is optionally prepared, for example, a patch or region of skin to be used is cleaned for sufficient light transmission and/or reflection. Respiratory-monitor 200 is placed on and attached to the subject (306), optionally mechanically secured to ensure sufficient and stable contact with the skin. For example, by a thimble-like structure in case of a finger, or by an elastic band or a strap with a fastener such as buckle or hooks-and-loops pair, or a removable adhesive patch.

In some embodiments, microphone 216 is separately attached to the subject, for example, near the mouth or on the throat, and coupled to the rest of respiratory-monitor by wires or wireless connection (e.g. Bluetooth).

Using user interface 220 (or as a default operation upon connecting respiratory-monitor 200), respiratory-monitor 200 begins to acquire signals which are verified for acceptability (308). For example, the signals are visually verified by showing on display 212a signal with lower and/or upper acceptable limits and if the signal is outside the limits, or the signal is noisy or irregular, or the signals notified to have too low amplitude or have too low signal to noise ratio (e.g. bad or low quality signal), then sensor 200 and/or contact thereof with the skin should be checked. Optionally or additionally, in some embodiments, the signals stored in buffer 204 (or in memory 210) are compared by processor 206 to a template or templates of an appropriate signal stored in memory 210 (e.g. a typical signal template and/or upper and lower limits templates) and/or the quality of the signal is assessed for regularity and noise, and processor 206 notifies the subject in case of non-acceptable signals, such as by display 212 and/or buzzer 214.

When the signals are acceptable respiratory-monitor 200 is set, typically by user interface 220 to start monitoring (310). Optionally an operation mode is set by user interface 220, such as continuous evaluation, periodic evaluation, display contents and/or formats, alarm type, record mode or any operational mode respiratory-monitor 200 supports.

Optionally, using user interface 220 operational limits are set so that system 200 activates buzzer 214 and/or vibrator 218 and/or displays notification on display 212 if the limits are breached.

In some embodiments, during monitoring respiratory-monitor 200 supervises the acquired signals for acceptability (see also above) and in case of insufficient signal quality respiratory-monitor 200 generates a notification and/on alert such as by user interface 220 or buzzer 214 or vibrator 218 (322).

It should be noted that setting for the subject age or state may be carried out at any phase such as after placing on the subject or just before monitoring is started.

In some embodiments, the working parameters of respiratory-monitor 200 can be manually modified or tuned (312) by user interface 220 in accordance with a physician's instructions or by any qualified person.

In some embodiments, respiratory-monitor 200 performs automatic tuning. For example, if due to respiration rate a mild or moderate respiratory insufficiency condition is evaluated while the other signals indicate normal or close to normal condition, respiratory-monitor 200 modifies the respiration rate condition (e.g. increases the threshold), such as within a prescribed (allowed) modification range coded in respiratory-monitor 200.

In some embodiments, the tuning is carried out while respiratory-monitor 200 is monitoring, or in some embodiments monitoring is temporarily suspended and resumed after the tuning is done (324).

In some embodiments, periodically and/or upon an event such as tuning, data pertaining to the monitoring is stored (314) during monitoring (326) for optional subsequent use. For example, during changes in respiratory status or during exacerbation of respiratory disease, parameters used for monitoring or events such as tuning are logged. The records are stored on respiratory-monitor 200 and/or other devices by communications (314), and used, for example, to analyze the subject disease/respiratory status, frequency of exacerbations and/or severity.

FIG. 2B illustrates a flowchart outlining actions during monitoring of assessment of respiratory status, according to exemplary embodiments of the invention, such as operation 310 of FIG. 2A.

A temporally varying hemodynamic waveform signal, which is optionally a PPG signal, is acquired (332) and blood $CO_2$ (334) is derived from it. For simplicity of the discussion, the temporally varying hemodynamic waveform signal is referred to, herein, as a $CO_2$ signal. This, although that at the moment it is acquired, the signal is not yet directly indicative of blood $CO_2$, but rather only at a later stage, when the derivation (334) is performed by way of computation.

Respiratory rate is obtained (336) from analyzing the $CO_2$ temporal waveform signal for peaks and valleys, optionally as part of a preliminary procedure to derive the blood $CO_2$. Optionally, respiratory rate is obtained by another procedure and/or device such as nasal temperature detector (or sensor).

$O_2$ saturation is obtained from a pulse oximeter, optionally and preferably integrated or linked or coupled with respiratory-monitor 200 (338). Heart rate is obtained (340) from the PPG signal of the $CO_2$-Meter, or from the $O_2$ temporal signal acquired by the oximeter, or from another sensor or probe that detects pulses on a peripheral blood vessel near the skin, or any other device appropriate for obtaining heart rate such as an ECG device or a microphone and processor to detect and analyze the heart sounds.

According to the values or blood $CO_2$, $O_2$ saturation respiratory and heart rate the respiratory condition (exacerbation) of the subject is determined, such as exemplified with respect to Tables 1-5 above. However, in some embodiments, the actual measured values may be displayed, in addition to or instead of the grading scale shown in the tables above. The actual values may be of help to the caregiver, in some scenarios.

Once the severity of the respiratory condition and/or exacerbation is determined, an appropriate notification is generated (344), such as audible alert and/or graphical and/or any other method appropriate or sufficient to draw the attention of the attending physician (in a hospital environment) or of the subject (or a guardian thereof, in a home setting).

The monitoring is repeated (350) until stopped such as manually or automatically, such as by a programmed operation duration or according to the subject respiratory condition.

In some embodiments, respiratory condition is determined after several prior interim determinations and an average (or other statistics or procedure) is carried out to obtain an exacerbation status.

In some embodiments, the order of operations 332-340 is not mandatory and may vary. In some embodiments, and in order to obtain a value or determine respiratory condition an operation in 332-340 may be repeated, optionally irrespective of the number of repetitions of other operations.

The signals (or values) of blood $CO_2$, $O_2$ saturation, respiratory and heart rate are given as a non-limiting example and additional signals or other values may be used, for example, invasive blood $CO_2$ results, respiratory rate, pulse rate and wheeze sound. In some embodiments, pulsus paradoxus is also used and, for example, may be estimated from blood pressure measurements during inspiration and expiration, or from the amplitude (or other) changes in the PPG signal.

Notification of Respiratory Condition

A respiratory-monitor, such as respiratory-monitor 200 of FIG. 1 referred below as a non-limiting example, notifies the subject (or guardian thereof) on the respiratory condition or exacerbation.

In some embodiments, the notification is provided on display 212 as an alphanumeric value such as 'MILD' or 'SEVERE', optionally or additionally, as a value such as between '0' for normal and '4' as critical. In some embodiments, according to the exacerbation the display is colored such as yellow for mild exacerbation, red for severe and yellow message on red background as critical, and green for normal. In some embodiments, the display flashes with a rate according to the exacerbation, optionally with accompanying 'beeps' or continuous sound.

In some embodiments, the notification is, or accompanied by vibrations, optionally repeated vibrations rate according to the exacerbation.

In some embodiments, the notification is, or accompanied by voice alert, such as 'call emergency' or 'contact a physician'.

In some embodiments, the notification of respiratory-monitor 200 is selectable, such as from a list, to match the language of the subject. In some embodiments, the notification of respiratory-monitor 200 is customizable such as in one country it is set, for example, to 'Call 911' and in another to 'Call 101'.

Mounting of the Device on the Subject

Figure 3A:
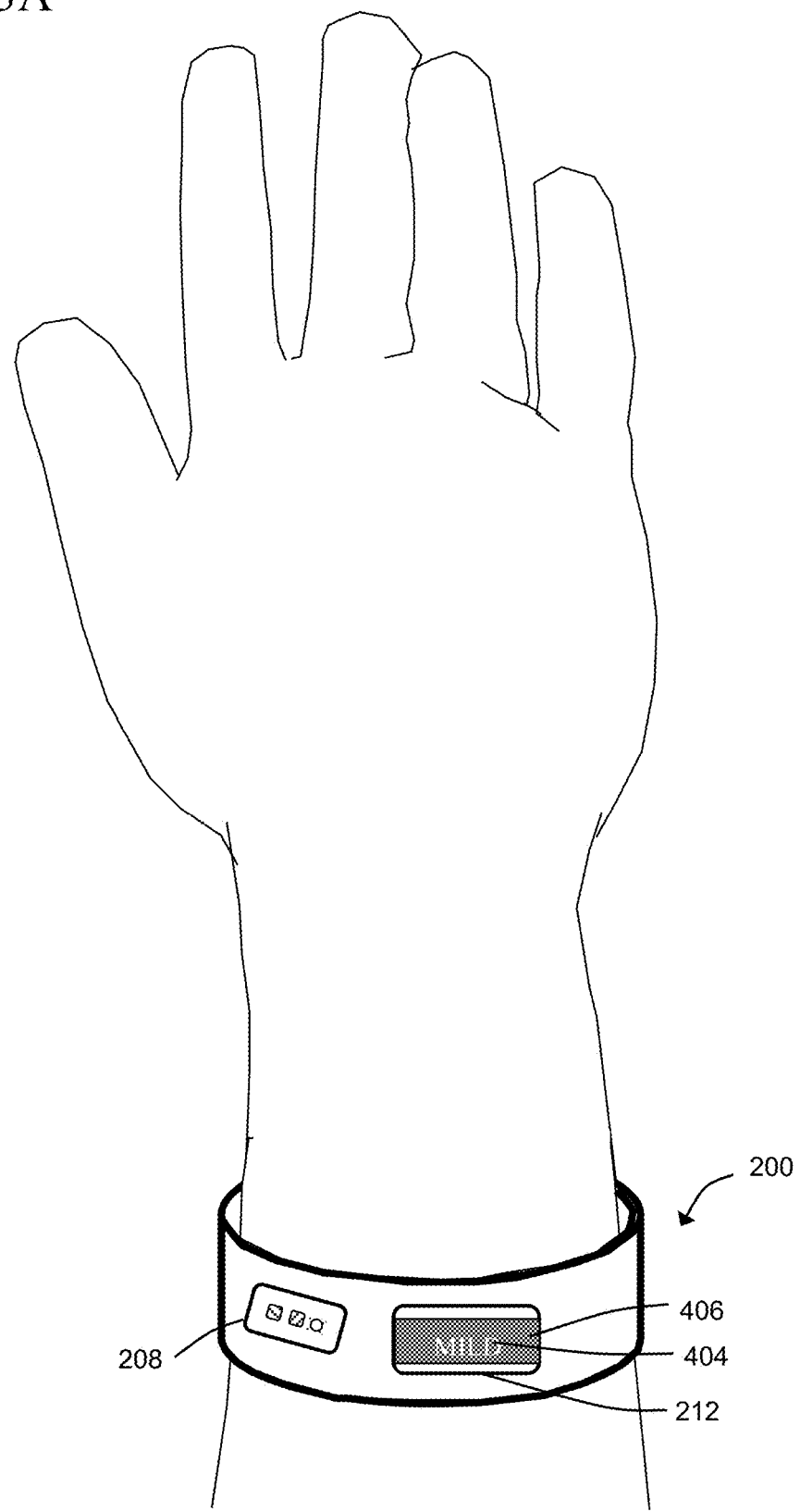
FIG. 3A schematically illustrates a respiratory-monitor disposed on a wrist, according to exemplary embodiments of the invention.

FIG. 3A schematically illustrates a respiratory-monitor, such as respiratory-monitor 200 of FIG. 1 referred below as a non-limiting example, disposed on a wrist according to exemplary embodiments of the invention. In such embodiments respiratory-monitor 200 comprises a $CO_2$ sensor and an $O_2$ sensor (or probes) 202c and 202o, respectively, a $CO_2$ sensor and an $O_2$ sensor (or probes) 202c and 202o, respectively, which are mounted on the internal side (towards the skin) of respiratory-monitor 200 and on the external side of respiratory-monitor 200 are mounted user interface 220 or part thereof, and optionally microphone 216. For example, manual input 208 and display 212 showing as an example a text message 404 on a colored or shaded background 406. A vibrator (not shown) may be disposed on the internal side of respiratory-monitor 200.

Figure 3B:
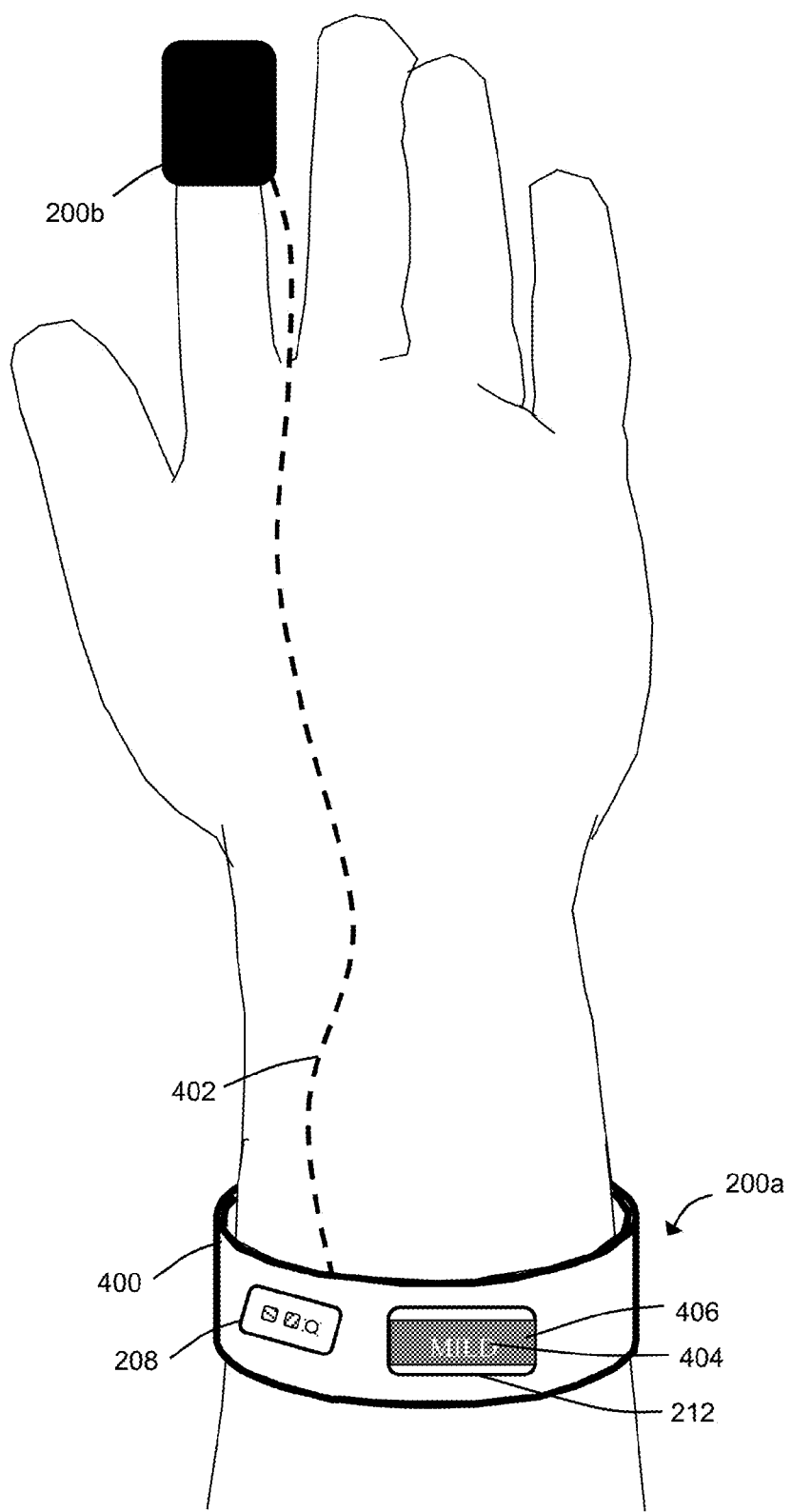
FIG. 3B schematically illustrates a respiratory-monitor disposed on a wrist while the probes are on a finger, according to exemplary embodiments of the invention.

FIG. 3B schematically illustrates a respiratory-monitor part 200a of respiratory-monitor 200 disposed on a wrist while another part 200b comprising one or more probes (or sensors) 200 is disposed on a finger, according to exemplary embodiments of the invention. Part 200a is typically a control part that allows setting and generates alerts while part 200b is typically the sensing or probing part, comprising a $CO_2$ sensor and an $O_2$ sensor (or probes) 202c and 202o, respectively, and optionally a microphone 216. Probes part 200b is connected to part 200a by a linkage such as wire 402 or by a wireless connection such as Bluetooth.

In some embodiments, respiratory-monitor 200 is mounted on a finger or disposed on any appropriate part of the subject.

In some embodiments, a part of respiratory-monitor 200 is mounted on the subject whereas another part of respiratory-monitor 200, typically for setting and/or alerts (e.g. control part), is mounted on a guardian of the subject, such as a parent of a child subject. The parts are connected such as by wires or wireless communications.

Figure 3C:
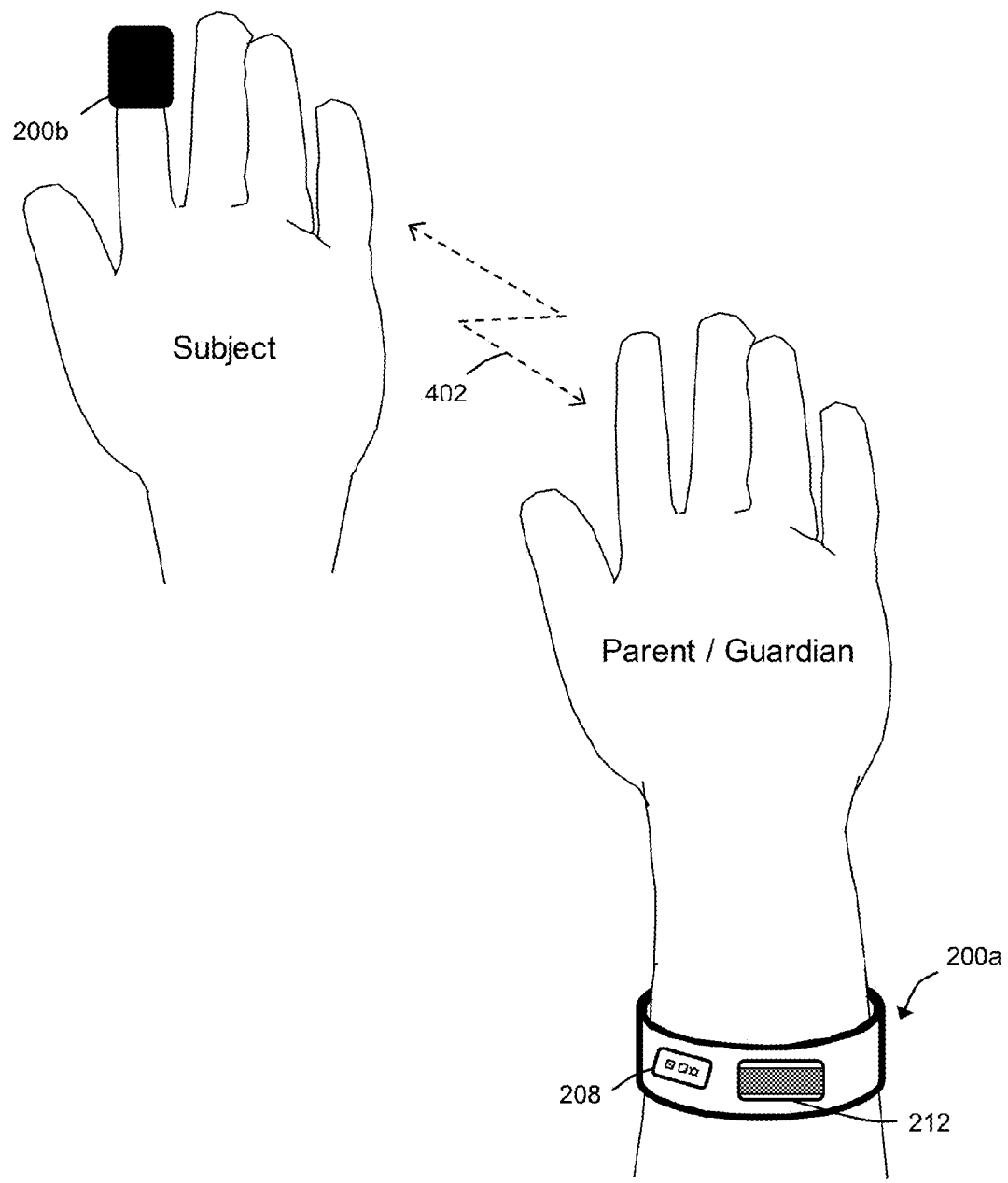
FIG. 3C schematically illustrates a respiratory-monitor where part of which is disposed on a subject and another part disposed on another person, according to exemplary embodiments of the invention.

FIG. 3C schematically illustrates a respiratory-monitor 200 where part of which 200b is disposed on a subject and another part 200a disposed on a guardian or parent (representing any person, such as paramedic), according to exemplary embodiments of the invention. Parts 200a and 200b are linked or coupled or connected by linkage 402, such as wire or any other method such as wireless connection.

In some embodiments, respiratory-monitor 200 is held on or attaches to a wrist or a finger by a thimble-like construction, or by a fastener such as elastic band, or buckle or hooks-and-loops or any appropriate fastener that is sufficient to acquire signals by the probes (or sensors) through the skin and to secure the device to the subject and/or guardian thereof.

Advantages

Some potential or probable advantages and benefits of respiratory-monitors as described above are:

1) Assessment or evaluation of respiratory status and/or exacerbation during medical conditions requiring monitoring, as they provide blood $CO_2$ (or close approximation thereof), contrary to alternative methods such as capnography which may be prone to lower accuracy due to arterial-alveolar gradient present during different pathological conditions. Capnography may be used simultaneously with the present respiratory monitor, so that the ability to detect a changing gradient will be a significant diagnostic feature.

2) They use a combination of $CO_2$ evaluation together with $O_2$ evaluation that provides an adequate clinical method to evaluate respiratory failure, as respiration involves an intricate balance between $O_2$, $CO_2$ and body metabolism.

3) They can help the physician determine when to use costly, invasive and more risky methods for respiratory monitoring, and thus make more cost-effective use of these medical devices and technologies.

4) They are small handy portable devices wearable on a person.

5) They are inexpensive to produce as compared to other devices available for measuring $CO_2$, and can be offered at an affordable price to patients who need a respiratory monitor.

6) They allow respiratory monitoring at home or trips outside and remote from medical facilities or during admission to a hospital or in first aid procedures.

7) They provide alerts that may be used to draw the attention of the subject (or guardian thereof) even during sleep.

8) They can be separated to a sensing part on a subject and control part on a guardian thereof.

9) They enable to report quantitative characteristics of the respiratory conditions, such as while consulting with a physician over the telephone.

Example

Figure 4:
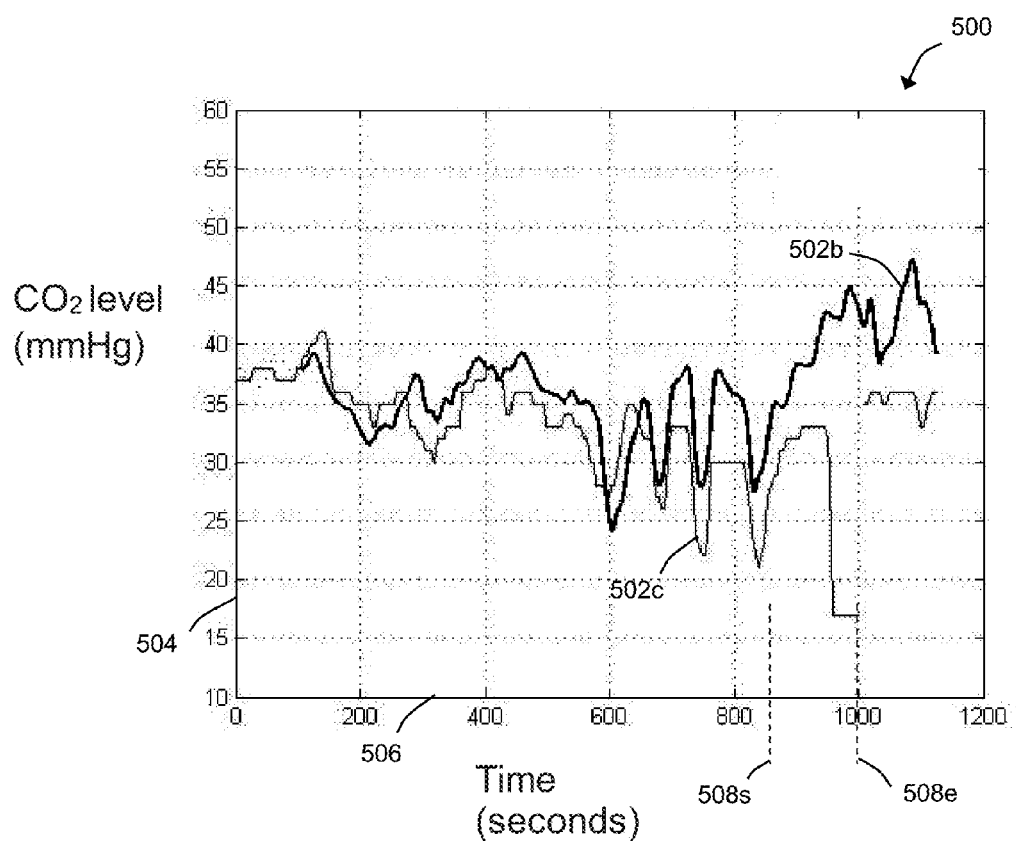
FIG. 4 illustrates a chart of responses to $CO_2$ of capnograph vs. a method of respiratory-monitor according to exemplary embodiments of the invention.
Figure 5:
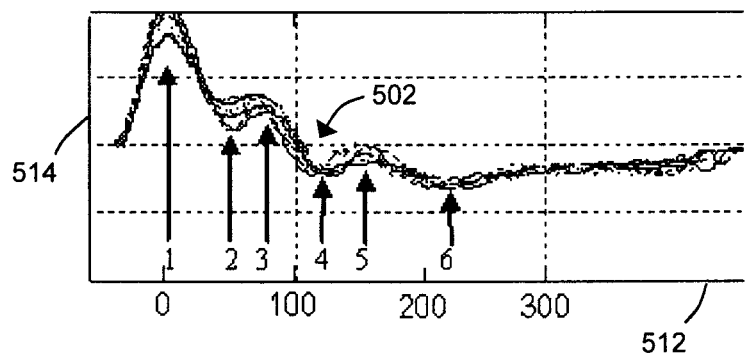
FIG. 5 illustrates the aligned and superimposed first temporal derivatives of normalized heart cycles of a waveform.
Figure 6:
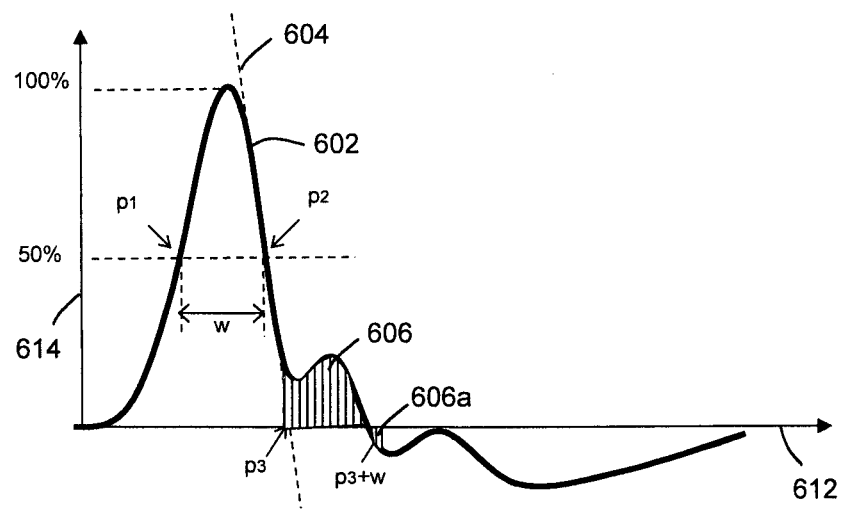
FIG. 6 illustrates a representative first temporal derivate of normalized heart cycles of a waveform.

FIG. 4 illustrates a chart 500 of responses to $CO_2$ of capnograph 502c vs. a method of respiratory-monitor for evaluation of blood $CO_2$ 502b according to exemplary embodiments of the invention. Vertical axis 504 represents $CO_2$ level (mmHg) and horizontal axis 506 represents breathing time (seconds). In a period of apnea between time indicated as 508s and 408e, the blood $CO_2$ 504b increases (insufficient breathing) while the capnograph readings 502c drop as the breathing and exhaling air flow is not sufficient, if at all, for the capnograph detection. The apnea simulates one of several respiratory conditions during which capnography measurements inherently deviate from the levels of arterial blood gases. On the other hand, the $CO_2$ measurement by the methods and apparatus described above ($CO_2$-Meter based on the principles disclosed in WO2009/144723) adequately agree with arterial blood $CO_2$.

Application of Embodiments of the Invention to the Monitoring of Different Medical Conditions The respiratory monitor of the various embodiments may be utilized, advantageously, to monitor one or more diseases and/or clinical conditions. Asthma is presented here as a main example, but the same principles are used in the monitoring of any other respiratory condition or medical condition which may cause respiratory failure. Other examples discussed herein include conditions where the risks of respiratory failure are large and well-known. However, due to the non-invasive nature of the present embodiments, they may be used widely in almost any condition, as the ability to detect respiratory changes greatly over-weighs inherent risks. These examples are:

Anesthesia
Surgical procedures—perioperative
Surgical procedures using CO2 insufflation
Intensive Care Unit treatment
ARDS (acute respiratory distress syndrome)
COPD
Asthma
Pain treatment (opioids)

Surgical Procedures:

Major surgical procedures such as cardiac bypass, thoracotomies, major laparotomies and transplant surgery are accompanied by profound changes in blood gases during surgery and in the peri-operative period. After general anesthesia and during recovery, respiration may be unstable due to the uneven release of anesthetics and medications which were accumulated in different body tissues during surgery. Therefore, the most accurate respiratory monitor should be used during surgery and recovery.

"The benefits of managing carbon dioxide concentration intraoperatively for the maintenance of cardiac output, tissue oxygenation, perfusion, intracranial pressure, and cerebrovascular reactivity are well defined." See Akca O., *Optimizing the intraoperative management of carbon dioxide concentration*, Curr Opin Anesthesiol. 2006 February; 19(1): 19-25.

"Respiratory depression is the most well-known and dangerous side effect of opioids". See Bouillon T., *Pharmacokinetic-Pharmacodynamic modeling of the respiratory depressant effect of alfentanil*, Anesthesiology 1999; 91:144-55.

Surgical Procedures Using $CO_2$ Insufflation:

Some surgical procedures make use of $CO_2$ insufflation; $CO_2$ tends to accumulate in body tissues, and may have adverse effects on respiration during and after surgery. Therefore, an accurate monitor which combines $CO_2$ levels with other parameters will be of value in these conditions. See Kerr K, Mills G. H., *Intra-operative and post-operative hypercapnia leading to delayed respiratory failure associated with transanal endoscopic microsurgery under general anesthesia*, British Journal of Anesthesia 86(4): 586-9 (2001).

Recovery after Surgery

During recovery from surgery, respiration may be unstable due to the uneven release of anesthetics and medications which were accumulated in different body tissues during the surgery. Therefore, the most accurate respiratory monitoring is needed during that stage. While most patients do well, it is of utmost importance to provide the earliest possible detection of respiratory deterioration, as soon as it starts to occur. Continuous, non-invasive $PaCO_2$ monitoring would provide that solution.

Intensive Care Unit Treatment:

Intensive Care Unit (ICU) patients are unstable, and must receive the best monitoring available to allow early diagnosis and intervention. For many unstable ICU patients, ABG sampling is performed periodically, every few hours or more often, depending on patient's condition. Most ICUs today own a point-of-care device for testing ABGs, to enable quicker diagnosis (as samples don't need to be transferred to a central lab to obtain $PaCO_2$ and other blood gas levels) and earlier, more efficient intervention. The present respiratory monitor, being a continuous, non-invasive $PaCO_2$ monitor (combined with additional vital parameters) will serve that purpose.

Emergency Room

Acute Respiratory Failure (ARF) is one of the major causes of consultation of elderly patients in emergency departments. ARF is a key symptom of most cardiac and respiratory diseases, such as cardiogenic pulmonary edema, exacerbation of chronic respiratory disease (including COPD, asthma, community acquired pneumonia) and of pulmonary embolism—all associated with high rates of morbidity and mortality. Naturally, respiratory status is also of very high importance in other critical conditions, such as major trauma. The present respiratory monitor, being a non-invasive $PaCO_2$ monitor combined with additional vital parameters can be very helpful to the ER physician, in assessing and following the respiratory status of a patient.

See Ray et al., *Acute respiratory failure in the elderly: etiology, emergency diagnosis and prognosis*, Critical Care 2006, 10:R82, and Yosefy C et al., *End tidal carbon dioxide as a predictor of the arterial PCO2 in the emergency department setting*, Emergency medical J 2004 September; 21(5):557-9.

Emergency Medical Services

Dynamic assessment of the ventilatory status of patients is of high importance in transport of patients by emergency medical services, as these patients can be very unstable. The present respiratory monitor, which combines non-invasive blood $CO_2$ measurement with additional vital parameters, would allow the paramedic or physician in charge to monitor respiration with the highest accuracy and detect changes in ventilation as they occur.

Procedural Sedation (Elective Surgery, Dentistry, Endoscopy, Intra-Vascular Procedures, Imaging, Etc.)

A growing trend is the performance of various surgical and non-surgical procedures under sedation. Sedation is achieved by intra-venous medications, and is aimed at reducing consciousness to a level that enables the surgical or non-surgical (for example, endoscopic or intra-vascular) procedure, without compromising natural breathing and without the need of mechanical ventilation. While the medications used are relatively safe, the procedure has unavoidable peaks of high (sedative) drug concentrations, which can cause periods of respiratory deterioration or even respiratory arrest.

The procedural sedation trend is aimed at reducing medical costs, and therefore, in many occasions, is performed without an expert anesthesiologist. A respiratory adverse event that goes unnoticed can develop into a catastrophic scenario, which the surgical/endoscopy expert may not be able to handle properly. Therefore, the use of an advanced respiratory monitor such as the present respiratory monitor, which provides early detection of changes in ventilation (which always precede the changes in oxygenation when natural breathing is involved) is of the highest importance in procedural sedation.

"It is well accepted that the principal negative impact of sedation and anesthesia is the compromise of respiratory function . . . . In the setting of sedation and anesthesia, hypoxia from hypoventilation is the most likely cause of hypoxemia." See American Society of Anesthesiologists Task Force on Sedation and Analgesia by Non-Anesthesiologists, *Practice guidelines for sedation and analgesia by non-anesthesiologists*. Anesthesiology. 2002; 96:1004-1017.

"In a prospective study by Vargo et al. of 49 adults undergoing gastroscopy with therapeutic intent, twice as many apnea episodes were diagnosed by capnography than by pulse oximetry or clinical observation. In another prospective study by Anderson et al. of 163 children, none of the apnea episodes that occurred in 24% of the endoscopic procedures was diagnosed by pulse oximetry or clinical observation alone." See Riphaus et al., *S3 Guideline: Sedation for Gastrointestinal Endoscopy* 2008. Endoscopy 2009; 41:787-815.

"Hypoventilation is the most significant complication attributable to sedation and general anesthesia." See Daniel E. Becker et al., *Respiratory Monitoring: Physiological and Technical Considerations*. Anesth Prog 56:14-22 2009.

Airway Emergencies:

The American Association for Respiratory Care guideline for management of airway emergencies lists arterial blood gas values among the parameters that need to be repeatedly assessed and monitored when treating airway emergencies.

A simple method for early detection of ventilation changes may enable early treatment of these changes, improve outcome by buying time, and prevent many of these ventilation changes from deteriorating into airway emergencies.

"Because the need for management of airway emergencies occurs unpredictably, personnel need to be able to respond with the appropriate equipment within 3 minutes, 24 hours/day, 7 days/week. Additionally, a person capable of airway management in the infant should be present at every delivery. A Level-II practitioner should be present at every high-risk delivery." See American Association for Respiratory Care, *AARC management of airway emergencies*, Respiratory Care 1995; 40(7):749-760

Head Injury:

$PaCO_2$ levels have major effects on brain blood flow, ranging from increased intracranial pressure (ICP) to extremely low cerebral blood flow leading to brain ischemia. Therefore, $PaCO_2$ should ideally be monitored in head injury patients, at all times from injury to recovery. As with previous applications, the use of capnography is limited here, as what affects cerebral blood vessels is arterial $CO_2$, and not lung $CO_2$ which may be very different from each other at this clinical scenario.

"In this selected population of patients with severe traumatic brain injury, measurements of $PETCO_2$ and $PaCO_2$ are not interchangeable. Further the $PaCO_2$-$PETCO_2$ gradient is not stable over time and cannot predict variations of $PaCO_2$. The use of $PETCO_2$ instead of $PaCO_2$ could be deleterious in patients in whom strict control of $PaCO_2$ values is required." See Seguin P et al., *The measurement of end-tidal carbon dioxide ($PETCO_2$) is not a significant parameter to monitor in patients with severe traumatic brain injury*. Can J Anesth. 2001 April; 48(4):396-400.

Pain Treatment:

Various clinical conditions (post-surgery, cancer, intractable pain of various origin) cause severe pain, which is treated by opioid or similar medications. In many instances today, these medications are semi-automatically injected per patient command to achieve optimal pain control (PCA—Patient Controlled Analgesia). While these are very effective for pain, adverse events include a significant risk of respiratory failure or even apnea—respiratory arrest (no breath). Therefore, it is highly advisable to monitor patients receiving such treatments with the best respiratory monitor available, to allow early detection of respiratory events and prompt intervention.

ARDS and ALI

Acute Respiratory Distress Syndrom (ARDS) is recognized as the most severe form of Acute Lung Injury (ALI), a form of diffuse alveolar injury. ARDS is defined as an acute condition characterized by bilateral pulmonary infiltrates and severe hypoxemia in the absence of evidence for cardiogenic pulmonary edema.

ARDS causes a marked increase in intrapulmonary shunt, leading to severe hypoxemia.

At the same time, this shunt makes interpretation of capnography $ETCO_2$ values clinically difficult.

As the condition progresses and the work of breathing increases, the partial pressure of carbon dioxide begins to rise.

The situation of patients with ARDS is far more critical than those with normal pulmonary function in the operating room (who are monitored for ventilation by assessing $ETCO_2$). $CO_2$ monitoring in the ICU may offer considerable insight for assessment and treatment. See "Partial pressure end-tidal carbon dioxide monitoring for patients with acute respiratory distress syndrome: effects of physiologic deadspace volume." M. J. Banner. In: J. B. Gravenstein et al. *Capnography: Clinical Aspects: carbon dioxide over time and volume*; Cambridge University Press 2004 ISBN 0-521-54034-8; p. 213-222.

A recent study of more than 200 patients with ALI or ARDS found that carbon dioxide clearance may be more important in determining clinical outcomes. Gattinoni and colleagues reported that among patients placed in the prone position, 28-day survival correlated inversely with changes in arterial carbon dioxide tension ($PaCO_2$). No association between survival and arterial oxygen tension ($Pao_2$) was found . . . . Carbon dioxide changes, more so than oxygen changes, relate to the anatomical status of the lung.

See Gainnier M, et al. Prone position and positive end-expiratory pressure in acute respiratory distress syndrome. *Crit. Care Med.* 2003; 31:2719-2726.

Application of Embodiments of the Invention to the Monitoring During Use of Different Medical Technologies Mechanical Ventilation:

Usually, medical procedures related to mechanical ventilation require accurate monitoring of oxygenation and ventilation. Examples include: As ventilation machines cannot know the metabolic status and oxygen requirements of a patient's body, inappropriate levels of ventilation may rather be the norm than the exception. The ability to continuously monitor $PaCO_2$ would allow better titration of mechanical ventilation during the entire course, from pre-intubation to post-extubation.

Also, to prevent Ventilator Induced Lung Injury (VILI), it is accepted today to use lower pressures and smaller tidal volumes as the standard treatment in patients with Acute Respiratory Failure. This actually means trying to use the lowest amount of ventilation which is still clinically acceptable. Such an approach, however, may result in hypercapnia; therefore, the ability to monitor $PaCO_2$ would be beneficial.

Transportation of ventilated patients involves hazards, either of hyperventilation or hypoventilation. The adequacy of ventilation should be monitored continuously; and actually, the "inability to adequately monitor patient's cardiopulmonary status during transport" is a contraindication to transport a mechanically ventilated patient. See AARC guideline for intrahospital transport of mechanically ventilated patients; Respiratory Care. June 2002 Vol 47 No. 6, 721-723. Therefore, a continuous $CO_2$ monitor will be of great value whenever a patient is before, during or after mechanical ventilation.

The AARC Guideline for Inhospital transport of mechanically ventilated patient lists, among several contra-indications to patient inhospital transport, "the inability to adequately monitor patient cardiopulmonary status during transport. One of the hazards of transport can be hyperventilation during manual ventilation, which may cause respiratory alkalosis, cardiac arrhythmias, and hypotension". Hyperventilation causes low values of PaCO2, and therefore may be readily identified by a continuous, non-invasive PaCO2 monitor. See American Association for Respiratory Care; in hospital transport of mechanically ventilated patient; Respiratory Care. June 2002 Vol 47 No. 6, 721-723.

"Interhospital transportation of critically ill and mechanically ventilated patients represents a common, yet difficult problem . . . . Patients who either require a tight control of $PCO_2$ or endured lengthy transportation could benefit greatly from the combination of expiratory capnography with mobile arterial blood gas analysis or the transcutaneous measurement of $PCO_2$." See Hinkelbein J., *Accuracy and precision of three different methods to determined $PCO_2$ ($PaCO_2$ vs. $PetCO_2$ vs. $PTCO_2$) during interhospital ground transport of critically ill and ventilated adults*. J Trauma 2008 July; 65(1):10-8.

Patients Breathing Supplemental Oxygen:

For patients who receive supplemental oxygen for any reason, pulse oximetry alone can be misleading, as it will show a decrease in oxygenation only very late after the hypoventilation event occurred. Therefore, in patients receiving supplemental oxygen, a non-invasive, continuous $PaCO_2$ monitor is important; and especially so in children, obese patients and pregnant patients.

"The potential benefit of supplemental oxygen must be weighed against the false sense of security conveyed to the clinician who does not monitor ventilation continuously and only monitors oxygenation by pulse oximetry." See Daniel E. Becker et al., *Respiratory Monitoring: Physiological and Technical Considerations*. Anesth Prog 56:14-22 2009.

General Medicine:

It should be understood that the medical conditions described above and below, do not limit themselves to certain medical wards or scenarios. As human beings rely on breathing for living, the risk of respiratory failure could happen almost everywhere—in the internal medicine department or in the surgical ward, in pediatric or neonatal departments (in these populations, and especially in neonates, sampling of arterial blood gases is very difficult; while the use of capnography is very limited due to the very low breathing tidal volumes), in Ob/Gyn departments, and for any person in whom a previously existing disease or another medical condition/technology increases the risk of respiratory failure or in whom undetected respiratory failure could go unnoticed for even a short time. For example, in the diagnosis and treatment of pulmonary embolization, shock, cardiac failure, and many other clinical situations—the use of $CO_2$ monitoring may be of diagnostic and therapeutic value. Therefore, the examples given only represent part of the potential scope of using the present device; and in fact, it could be used in almost any medical scenario within the hospital, in community medical services, emergency medical services, and by the individual patient at home, work and leisure.

Application of Embodiments of the Invention to Different Respiratory Conditions

COPD—Chronic Obstructive Pulmonary Disease:

Arterial blood gas sampling and analysis is helpful in assessing the severity of a COPD exacerbation. It properly assesses the degree of hypoxemia (as compared with indirect measurement by pulse oximetry) and hypercarbia, and adds valuable information to identify patients that are likely to require additional mechanical ventilatory support. See McCrory D C, Brown C, Gelfand S E, et al, *Management of acute exacerbations of COPD: a summary and appraisal of published evidence*. Chest 2001, 119:1190-1209.

Exacerbations of COPD are characterized by severe hypoxemia and hypercapnia. See Barbera J A et al. *Mechanisms of worsening gas exchange during acute exacerbations of chronic obstructive pulmonary disease*. European Respiratory Journal 1997; 10:1285-1291.

Arterial Carbon Dioxide tension and breathing rate were statistically different between all levels of exacerbation severity and between in- and out-patient settings in COPD. Arterial carbon dioxide and respiration rate varied in a consistent manner with exacerbation severity and patient setting. See Franciosi L G et al., *Markers of Exacerbation Severity in Chronic Obstructive Pulmonary Disease*, Respiratory Research 2006, 7:74.

A table grading the severity of COPD exacerbations is suggested by Burge et al., *COPD exacerbations: definitions and classifications*. Eur Respir J Suppl. 2003 June; 41:46s-53s. Such a table may be used for fine-tuning the definitions of tables 1-5 for accurate applicability to COPD patients.

The device may be used for early detection of COPD exacerbations and their follow-up. Disease management is highly dependent on $CO_2$ values, and a combined device will provide better monitoring and treatment for these patients.

Asthma

Following is a detailed example of how the present respiratory monitor is used for monitoring acute exacerbations of asthma. Using similar principles, the present respiratory monitor may be modified to monitor other medical conditions, as listed above and any other condition in which respiratory monitoring is of importance.

Asthma is a widespread disease that might develop acute conditions (exacerbation). In the early stages of exacerbation self-medicating (e.g. broncho-dilator inhalations at increasing dosages and later also oral corticosteroids) are typically used, and according to the situation a physician or an emergency medical facility might be needed.

Though acute asthma attacks pose a potential risk of respiratory deterioration, and though hand-held peak-flow meters may be used to provide some suggestion of the respiratory state, yet just subjective feelings and observations are typically considered when the subject is at home or distant from medical facilities.

The sooner an asthma attack is treated, the likelihood of deterioration into a severe exacerbation decreases, and smaller amounts of medications may be needed, and hospitalization may be prevented. However, over-treatment has adverse effects, and frequent referrals to medical evaluations could be distressing.

In case of children the parents or caretakers typically encounter further difficulties as children may not describe their symptoms accurately nor properly use flow-meters, thus adding to the diagnostic difficulties and possibly worsening the disease management.

PCT Published Patent Application WO2002/45566 discloses monitoring, diagnosing and treating at least one medical respiratory condition such as asthma where $CO_2$ level is acquired by a capnograph. However, while readings of a capnograph (e.g. $EtCO_2$) generally correlate with $CO_2$ level in the blood in health, in asthmatic conditions the readings can deviate from the blood $CO_2$, as disclosed, for example, in *J Trauma.* 2008 July; 65(1): 10-8, or *Acad Emerg Med.* 2007 December; 14(12): 1135-40 or *Br Med J (Clin Res Ed)*. 1984 Jun. 23; 288(6434): 1870-2.

Possibly, physiological mechanisms known as 'shunting' and 'ventilation/perfusion mismatch' cause constriction of pulmonary blood vessels in lung areas experiencing low oxygen levels, increasing the difference between blood $CO_2$ level and exhaled air $CO_2$ level (arterial—alveolar gradient) and reducing the correlation between $ETCO_2$ levels and the clinically meaningful blood $CO_2$ level.

See, for example, Garay S, Kamelar D (1989), "*Pathophysiology of trauma-associated respiratory failure*", in Hood R M, Boyd A D, Culliford A T, *Thoracic Trauma*. Philadelphia: Saunders. pp. 328-332. ISBN 0-7216-2353-0, or Fraser, Robert (1988), *Diagnosis of Diseases of the Chest*. Philadelphia: Saunders. pp. 139. ISBN 0-7216-3870-8, or J. B. Gravenstein et al. *Capnography: Clinical Aspects: carbon dioxide over time and volume*; Cambridge University Press 2004 ISBN 0-521-54034-8

The Global Initiative for Asthma (www.ginasthma.com) *Global Strategy for Asthma Management and Prevention* 2008 (hereinafter 'GINA') and *National Institutes of Health publication No 97-4051, Guidelines for the Diagnosis and Management of Asthma* 2007, (www.nhlbi.nih.gov/guidelines/asthma/asthgdln.pdf) (hereinafter 'NIH') provide some guidelines for determination of asthma condition. However, some of the parameters (signals) cited in the guidelines are not generally accessible outside medical facilities or without specialized equipment and correlation of several different values or observations are required to determine or assess the asthma condition.

Based on interrelation between signals due to the physiological differences in the response of vascular beds in different body organs or tissues, and/or based on distinctive temporal behavior of a signal, an apparatus described in international application PCT/IL2009/000530 provides blood $CO_2$ contrary to capnograph that may not or does not adequately correlate blood $CO_2$ during asthma. On the other hand the apparatus is non-invasive contrary to invasive methods to acquire blood $CO_2$, such as blood samples or intra-arterial $CO_2$ analyzer.

See, for example, Garay S, Kamelar D (1989), "*Pathophysiology of trauma-associated respiratory failure*", in Hood R M, Boyd A D, Culliford A T, *Thoracic Trauma*. Philadelphia: Saunders. pp. 328-332. ISBN 0-7216-2353-0, or Fraser, Robert (1988), *Diagnosis of Diseases of the Chest*. Philadelphia: Saunders. pp. 139. ISBN 0-7216-3870-8, or J. B. Gravenstein et al., *Capnography: Clinical Aspects: carbon dioxide over time and volume*; Cambridge University Press 2004 ISBN 0 521 54034 8

Accordingly, an aspect of the invention relates to assessment or evaluation of asthma condition in a subject based on blood $CO_2$ using non-invasive apparatus and/or methods.

In some embodiments, the device and methods of the aforementioned PCT Publication No. WO2009/144723 and variations thereof (hereinafter also '$CO_2$-Meter') are modified and/or augmented to acquire additional signals such as $O_2$ level (e.g. saturation), respiratory rate, airflow rate, heart rate and/or wheeze sound, or close approximations thereof, and use the additional signals to evaluate or assess asthma conditions. In some embodiments, the additional signals are also acquired non-invasively.

In some embodiments, the asthma condition is evaluated according to accepted or recommended guidelines such as of GINA or NIH.

In some embodiments, the device can be manually adjusted to adapt to age groups of subjects (e.g. infants, children or elderly subjects), and optionally to the clinical situation of the subject (e.g. after trauma or medical history). Optionally or additionally, the device may be adjusted to adapt according to the behavior or symptoms of a particular subject during asthma in order to avoid missing risky conditions and/or to avoid false alarms.

In some embodiments, under certain asthma conditions or circumstance, the device can be manually set to relate occurring situations to particular indications, and based on such settings the device may optionally adjust working parameters thereof for future operations. The device stores in memory thereof, or sends to other resources, events that occurred during the operation, such as a determination of asthma exacerbations, corresponding working parameters, or change of settings or any value that might be helpful for future analysis of the subject ongoing conditions and/or the device operation ('recording', 'trending').

In some embodiments, based on past results and/or trending the device may adjust to varying situations ('learning').

In some embodiments, the device is equipped with communication apparatus providing telemedicine capabilities and other remote operations.

In typical embodiments the apparatus is a battery operated portable device that can be worn on the subject, such as on or around an arm. The device provides indications as to the assessment or evaluation of asthma condition of the subject such as audible and/or graphical and/or color and/or alphanumeric notifications, as well as other alerts such as vibrations. In some preferred embodiments the device is suitable for personal use at home or on travel as well as for ambulatory and first aid use.

As an exemplary guideline, reference is made to GINA (GINA Report Global Strategy for Asthma Management and Prevention, updated 2008) and to Table-7 below which is derived from GINA (collectively referred to as 'GINA').

TABLE 7

| Grade: | Normal 0 | Mild 1 | Moderate 2 | Severe 3 | Critical 4 |
|---|---|---|---|---|---|
| Respiratory rate (breaths/min) | Normal (10-14) | Increased | Increased | Often > 30/min | Weak, unstable |
| Heart rate (pulse/min) | Normal (60-100) | <100 | 100-120 | >120 | <60 |
| $PaCO_2$ | Normal (36-44) | <45 mmHg (typ. 30-35) | <45 mmHg (typ. 36-38) | Normal - pseudo (typ. 39-44) | >45 mmHg possible respiratory failure | >50 mmHg |
| $SaO_2\%$ | Normal (>95%) | >95% | 91-95% | <90% | <<90% |

Status is shown across columns.

In Table-7 the asthma exacerbations (or status thereof) are coded or mapped into grades, where normal is coded as grade 0, mild as 1, moderate as 2, severe as 3 and imminent respiratory arrest (critical) as grade 4.

As an example an adult subject is monitored for $PaCO_2$, $SaO_2$, respiratory rate and heart rate as exemplary signals.

Assuming the values are obtained as shown in Table-8 below.

TABLE 8

| Signal | Value | Unit | Grade |
|---|---|---|---|
| Heart rate | 130 | PPM | 3 |
| Respiratory rate | 35 | BPM | 3 |
| $SaO_2$ | 89 | % | 3 |
| $PaCO_2$ | 47 | mmHg | 3 |

The grades are averaged providing a combined grade of 3 (severe exacerbation).

As another example, assuming the values are obtained as shown in Table-9 below, where $PaCO_2$ is 40 which is typically normal.

TABLE 9

| Signal | Value | Unit | Grade |
| --- | --- | --- | --- |
| Heart rate | 130 | PPM | 3 |
| Respiratory rate | 35 | BPM | 3 |
| SaO$_2$ | 89 | % | 3 |
| PaCO$_2$ | 40 | mmHg | 0 |

Averaging the grades the combined grade is 2.25, indicating an approximate moderate exacerbation.

However, considering the other signals a seemingly normal value of PaCO$_2$ may be misleading. Thus, as the other signals are of a quite high grade (severe exacerbation) the PaCO$_2$ value is considered as a pseudo-normal value (e.g. changing from low to high values when respiratory muscles are starting to fatigue) and assigned the respective severe grade, namely a grade of 3, as in Table-10 below.

TABLE 10

| Signal | Value | Unit | Grade |
| --- | --- | --- | --- |
| Heart rate | 130 | PPM | 3 |
| Respiratory rate | 35 | BPM | 3 |
| SaO$_2$ | 89 | % | 3 |
| PaCO$_2$ | 40 | mmHg | 3 |

In such a case the combined grade is 3 indicating an approximate severe exacerbation.

In some embodiments, a signal may be considered more significant than others. For example, according to the clinical condition and history of the subject, such as having had respiration arrests, the PaCO$_2$ is assigned a weight of 2, and the values of Table-10 are given now as in Table-11 below.

TABLE 11

| Signal | Value | Unit | Grade |
| --- | --- | --- | --- |
| Heart rate | 130 | PPM | 3 |
| Respiratory rate | 35 | BPM | 3 |
| SaO$_2$ | 89 | % | 3 |
| PaCO$_2$ | 40 | mmHg | 3 × 2 |

The combined grade is now 3.75 indicating a worsening severe condition that may result in respiratory arrest.

A signal weight or significance may also depend on a recent trend or history. For example, in case a recent trend of 2 hours sampling rate provides successive PaCO$_2$ values of 30, 30, 35, 40 (in mmHg, continuously rising), and corresponding respiratory rates are 25, 25, 25, 25 (in BPH, continuously high) and the corresponding SaO$_2$ values are 98, 98, 95, 93 (in percent, continuously declining), then the PaCO$_2$ weight is increased (e.g. doubled) or assigned a value depending on the other signals (e.g. one above the average thereof).

In some embodiments, the grade assigned to a signal depends on the value with respect to range thereabout. For example, referring to Table-7 above, SaO$_2$ is 89 which is considered as a severe condition, yet it is just slightly below a moderate condition value. Thus, taking the range 90-95 to correspond the range of grades 2-3 (or any other plausible correspondence), the value of 89 results in grade 3.20, and Table-7 will be modified accordingly to Table-12 below.

TABLE 12

| Signal | Value | Unit | Grade |
| --- | --- | --- | --- |
| Heart rate | 130 | PPM | 3 |
| Respiratory rate | 35 | BPM | 3 |
| SaO$_2$ | 89 | % | 3.2 |
| PaCO$_2$ | 47 | mmHg | 3 |

The combined grade is now 3.05 indicating a severe exacerbation.

Asthma-Monitor Device

The CO$_2$-Meter, or a variation thereof, is integrated with other apparatus to form a monitor device for asthma conditions (hereinafter also 'asthma-monitor').

In some embodiments, the asthma-monitor comprises a CO$_2$-Meter and a pulse oximeter, or any elements or parts thereof, such as light photoplethysmography (PPG) probe or probes. Optionally, the asthma-monitor comprises or is coupled or linked with a microphone for wheeze detection and corresponding voice or audio processor or analyzer.

In some embodiments, the asthma-monitor comprises a memory or storage device or devices (memory) and at least one processor coupled to the memory or part thereof. A memory portion, preferably a non-volatile memory, is coded with or comprises or embodies a program or part thereof readable and executable by the one or more processors to control the apparatus of the asthma-monitor and carry out the monitoring and evaluation of the asthma conditions and any function of the asthma-monitor.

In some embodiments, the at least one processor comprises one or more of a DSP or an ASIC or any customized or special purpose or general purpose processor. Optionally the asthma-monitor comprises analog to digital converter to adapt analog signals for digital processing.

In some embodiments, a memory portion is allocated for variables and/or constants that participate in the asthma-monitoring (work parameters or parameters). Optionally, a memory portion is allocated for recording past values such as past events, past evaluations or past signals (trending).

In some embodiments of the invention, the asthma-monitor is, preferably, an integrated portable unit sufficiently small and lightweight to be worn on a subject, such as on the wrist or arm, or on a belt, or as part of clothes or on a forehead strap, even by children. In some embodiments, the sensors are attached to fingers or to other body sites where they are possibly hidden under clothing. Preferably the asthma-monitor is self powered such as by a battery or by a hand-driven generator that loads a capacitor.

In some embodiments, the asthma-monitor comprises user interface for manual inputs or settings, for example, buttons or touch screen or any other mechanism such as dials. In some embodiments, the asthma-monitor comprises user interface for asthma indications and/or alerts or any other data, for example, audio sounds, voice alerts, alphanumerical display, graphical or any other displays such as color and/or grayscale coded alerts or charts relatively depicting the exacerbation or any other interaction such as vibrations.

Preferably the asthma-monitor is sufficiently small for stationary or home or mobile use such as in ambulances, and preferably lightweight to be wearable for home or outside use, such as on travel.

Reference will now be made, again, to FIGS. 1 through 4, this time while describing them in the context of asthma monitoring. For simplicity of presentation, and prevention of figure redundancies, the same figures are reused for two different contexts, that of the more general medical condition monitoring and that of asthma monitoring.

FIG. 1 schematically illustrates a block diagram of an asthma-monitor (or system) 200, illustrating with arrows the main control linkages between components thereof, according to exemplary embodiments of the invention.

Asthma-monitor 200 comprises or is connected to sensors (or probes) 202c and 202o for acquiring $CO_2$ and $O_2$ signals, such as $PaCO_2$ and $SaO_2$, respectively, or close approximations thereof. Optionally, system 200 comprises or is connected to additional sensor or sensors represented as 202z and marked with dashed outline, for example, heart rate or respiratory rate sensor or other sensors such as a moisture sensor to assess the agitation state of a subject (see for example GINA and Table-1). Typically and preferably, sensors 202 are attached on or approximate to the skin of the monitored subject (non-invasive detection). In some embodiments, at least sensors 202c and 202o comprise or are implemented as or constitute photoplethysmography probes, and optionally sensors 202c and 202o are integrated or constructed as a combined probe.

It should be noted that $CO_2$ or $O_2$ sensors, 202c and 202o respectively, are used to acquire signals related to $CO_2$ and $O_2$ but are not necessarily particularly sensitive to $CO_2$ or $O_2$, and are denoted as such herein for clarity. For example, in some cases the same apparatus such as light source and radiation detector can be used for both $CO_2$ and $O_2$ (and possibly other constituents) where the difference is in the circuitry or program employed to process the acquired signals.

In some embodiments, system 200 comprises a microphone 216, or alternatively a sensor for sound vibrations (hereinafter 'microphone') to sense wheeze sounds and/or optionally to sense heart rate.

The system operation is carried out by a processor (or processors) 206 according to a program or programs and data stored in memory 210. The program operation is controlled or regulated by user input elements 208 of user interface 220, such as buttons or dials interface or data entered therethrough. The assessed asthma conditions are indicated on display 212 of user interface 220, along with other data such as feedback to elements 208. Optionally, input elements 208 and display 212 are combined, such as a touch-screen. In some embodiments, display 212 comprises other visual elements such as one or more LED lights.

Memory 210 typically comprises read-only memory and/or read/write memory, optionally comprising portions of non-volatile memory. The output of sensor 202 and microphone 216 is obtained (acquired) via input ports of processor 206 (or other ports) into an interface or buffer 204 for storing the raw data that is further processed. Optionally, interface 204, or part thereof, is comprised in memory 210 or in a module of processor 206, and buffer or interface 204 represents any apparatus for interfacing between a peripheral device (or sensor) and memory 210 and/or processor 206, such as Analog-to-Digital converter (ADC) that is optionally multiplexed between a plurality of sensors 202.

In some embodiments, asthma-monitor 200 is powered by a power supply connected to mains socket. Preferably, asthma-monitor 200 is a portable device powered by a battery.

In some embodiments, asthma-monitor 200 comprises a buzzer 214 representing also any sound indication and/or alarm equipment or mechanism, and in some embodiments system 200 comprises a vibrator 218 representing any equipment or mechanism for tactile indication and/or alarm.

In some embodiments, buzzer 214 or vibrator are adapted (or set or tuned) to awake the subject or guardian thereof.

In some embodiments, asthma-monitor 200 comprises communication apparatus to connect to an auxiliary device with notification and/or human or user interface such as 220 or part thereof for use by another person such as guardian of the subject.

In some embodiments, asthma-monitor 200 is equipped with or comprises apparatus to enable uploading data from asthma-monitor 200 (e.g. stored records, see also below) or to enable downloading of data and/or programs such as to upgrade or adapt asthma-monitor 200 to different subjects.

In some embodiments, asthma-monitor 200 is equipped with apparatus for telemedicine, for example, enabling a remote physician to assess the condition of the subject and/or offer a treatment.

FIG. 2A illustrates a flowchart 300 concisely outlining actions for assessment of asthma exacerbations, according to exemplary embodiments of the invention. In the following discussion reference to asthma-monitor 200 of FIG. 1 is implied as a non-limiting example.

Typically asthma symptoms (and normal ranges of physiological parameters) vary between age groups (see for example, GINA and Table-1 for respiratory rate). Accordingly, by using user interface 220 asthma-monitor 200 is set for the subject age (302). For example, by setting the age the program is directed to use a set of parameters respective to the age for assessing the asthma condition. In some embodiments, the medical history or clinical state of the subject are considered and in addition to age representative states are selected by user interface 220. Optionally or alternatively, working parameters of the program are modified by user interface 220 to reflect the subject state.

A suitable organ or tissue for placing asthma-monitor 200 is located on the subject to be monitored so that sensors 202 would acquire sufficient signals in terms such as amplitude and/or signal to noise ratio (304). The skin is optionally prepared, for example, a patch or region of skin to be used is cleaned for sufficient light transmission and/or reflection. Asthma-monitor 200 is placed on and attached to the subject (306), optionally mechanically secured to ensure sufficient and stable contact with the skin. For example, by a thimble-like structure in case of a finger, or by an elastic band or a strap with a fastener such as buckle or hooks-and-loops pair, or a removable adhesive patch.

In some embodiments, microphone 216 is separately attached to the subject, for example, near the mouth or on the throat, and coupled to the rest of asthma-monitor by wires or wireless connection (e.g. Bluetooth).

Using user interface 220 (or as a default operation upon connecting asthma-monitor 200), asthma-monitor 200 begins to acquire signals which are verified for acceptability (308). For example, the signals are visually verified by showing on display 212 a signal with lower and/or upper acceptable limits and if the signal is outside the limits, or the signal is noisy or irregular, or the signals notified to have too low amplitude or have too low signal to noise ratio (e.g. bad or low quality signal), then sensor 200 and/or contact thereof with the skin should be checked. Optionally or additionally, in some embodiments, the signals stored in buffer 204 (or in memory 210) are compared by processor 206 to a template or templates of an appropriate signal stored in memory 210 (e.g. a typical signal template and/or upper and lower limits templates) and/or the quality of the signal is assessed for regularity and noise, and processor 206 notifies the subject in case of non-acceptable signals, such as by display 212 and/or buzzer 214.

When the signals are acceptable asthma-monitor 200 is set, typically by user interface 220 to start monitoring (310). Optionally an operation mode is set by user interface 220, such as continuous evaluation, periodic evaluation, display contents and/or formats, alarm type, record mode or any operational mode asthma-monitor 200 supports.

Optionally, using user interface 220 operational limits are set so that system 200 activates buzzer 214 and/or vibrator 218 and/or displays notification on display 212 if the limits are breached.

In some embodiments, during monitoring asthma-monitor 200 supervises the acquired signals for acceptability (see also above) and in case of insufficient signal quality asthma-monitor 200 generates a notification and/on alert such as by user interface 220 or buzzer 214 or vibrator 218 (322).

It should be noted that setting for the subject age or state may be carried out at any phase such as after placing on the subject or just before monitoring is started.

In some embodiments, the working parameters of asthma-monitor 200 can be manually modified or tuned (312) by user interface 220 in accordance with a physician's instructions or by any qualified person.

In some embodiments, asthma-monitor 200 performs automatic tuning. For example, if due to respiration rate a mild or moderate asthma exacerbation is evaluated while the other signals indicate normal or close to normal condition, asthma-monitor 200 modifies the respiration rate condition (e.g. increases the threshold), such as within a prescribed (allowed) modification range coded in asthma-monitor 200.

In some embodiments, the tuning is carried out while asthma-monitor 200 is monitoring, or in some embodiments monitoring is temporarily suspended and resumed after the tuning is done (324).

In some embodiments, periodically and/or upon an event such as tuning, data pertaining to the monitoring is stored (314) during monitoring (326) for optional subsequent use. For example, asthma attacks or exacerbations, parameters used for monitoring or events such as tuning are logged. The records are stored on asthma-monitor 200 and/or other devices by communications (314), and used, for example, to analyze the subject asthma progress, frequency of exacerbations and/or severity.

FIG. 2B illustrates a flowchart outlining actions during monitoring of assessment of asthma exacerbations, according to exemplary embodiments of the invention, such as operation 310 of FIG. 2A.

A temporally varying hemodynamic waveform signal, which is optionally a PPG signal, is acquired (332) and blood $CO_2$ (334) is derived from it. For simplicity of the discussion, the temporally varying hemodynamic waveform signal is referred to, herein, as a $CO_2$ signal. This, although that at the moment it is acquired, the signal is not yet directly indicative of blood $CO_2$, but rather only at a later stage, when the derivation (334) is performed by way of computation.

Respiratory rate is obtained (336) from analyzing the $CO_2$ temporal waveform signal for peaks and valleys, optionally as part of a preliminary procedure to derive the blood $CO_2$. Optionally, respiratory rate is obtained by another procedure and/or device such as nasal temperature detector (or sensor).

$O_2$ saturation is obtained from a pulse oximeter, optionally and preferably integrated or linked or coupled with asthma-monitor 200 (338). Heart rate is obtained (340) from the PPG signal of the $CO_2$-Meter, or from the $O_2$ temporal signal acquired by the oximeter, or from another sensor or probe that detects pulses on a peripheral blood vessel near the skin, or any other device appropriate for obtaining heart rate such as an ECG device or a microphone and processor to detect and analyze the heart sounds.

According to the values or blood $CO_2$, $O_2$ saturation respiratory and heart rate the asthma condition (exacerbation) of the subject is determined, such as exemplified with respect to Tables 1-5 above.

Once an asthma exacerbation is determined, an appropriate notification is generated (344), such as audible alert and/or graphical and/or any other method appropriate or sufficient to draw the attention of the subject (or guardian thereof).

The monitoring is repeated (350) until stopped such as manually or automatically, such as by a programmed operation duration or according to the subject asthma condition.

In some embodiments, asthma condition is determined after several prior interim determinations and an average (or other statistics or procedure) is carried out to obtain an exacerbation status.

In some embodiments, the order of operations 332-340 is not mandatory and may vary. In some embodiments, and in order to obtain a value or determine asthma condition an operation in 332-340 may be repeated, optionally irrespective of the number of repetitions of other operations.

The signals (or values) of blood $CO_2$, $O_2$ saturation respiratory and heart rate are given as a non-limiting example and additional signals or other values may be used, for example, blood $CO_2$, respiratory rate, pulse rate and wheeze sound. In some embodiments, pulsus paradoxus is also used and, for example, may be estimated from blood pressure measurements during inspiration and expiration, or from the amplitude (or other) changes in the PPG signal.

An asthma-monitor, such as asthma-monitor 200 of FIG. 1 referred below as a non-limiting example, notifies the subject (or guardian thereof) on the asthma condition or exacerbation.

In some embodiments, the notification is provided on display 212 as an alphanumeric value such as 'MILD' or 'SEVERE', optionally or additionally, as a value such as between '0' for normal and '4' as critical. In some embodiments, according to the exacerbation the display is colored such as yellow for mild exacerbation, red for severe and yellow message on red background as critical, and green for normal. In some embodiments, the display flashes with a rate according to the exacerbation, optionally with accompanying 'beeps' or continuous sound.

In some embodiments, the notification is, or accompanied by vibrations, optionally repeated vibrations rate according to the exacerbation.

In some embodiments, the notification is, or accompanied by voice alert, such as 'call emergency' or 'contact a physician'.

In some embodiments, the notification of asthma-monitor 200 is selectable, such as from a list, to match the language of the subject. In some embodiments, the notification of asthma-monitor 200 is customizable such as in one country it is set, for example, to 'Call 911' and in another to 'Call 101'.

FIG. 3A schematically illustrates an asthma-monitor, such as asthma-monitor 200 of FIG. 1 referred below as a non-limiting example, disposed on a wrist according to exemplary embodiments of the invention. In such embodiments asthma-monitor 200 comprises a $CO_2$ sensor and an $O_2$ sensor (or probes) 202c and 202o, respectively, a $CO_2$ sensor and an $O_2$ sensor (or probes) 202c and 202o, respectively, which are mounted on the internal side (towards the skin) of asthma-monitor 200 and on the external side of asthma-monitor 200 are mounted user interface 220 or part thereof, and optionally microphone 216. For example, manual input 208 and display 212 showing as an example a text message 404 on a colored or shaded background 406. A vibrator (not shown) may be disposed on the internal side of asthma-monitor 200.

FIG. 3B schematically illustrates an asthma-monitor part 200a of asthma-monitor 200 disposed on a wrist while another part 200b comprising probes (or sensors) 200 is disposed on a finger, according to exemplary embodiments of the invention. Part 200a is typically a control part that allows setting and generates alerts while part 200b is typically the sensing or probing part, comprising a $CO_2$ sensor and an $O_2$ sensor (or probes) 202c and 202o, respectively, and optionally a microphone 216. Probes part 200b is connected to part 200a by a linkage such as wire 402 or by a wireless connection such as Bluetooth.

In some embodiments, asthma-monitor 200 is mounted on a finger or disposed on any appropriate part of the subject.

In some embodiments, a part of asthma-monitor 200 is mounted on the subject whereas another part of asthma-monitor 200, typically for setting and/or alerts (e.g. control part), is mounted on a guardian of the subject, such as a parent of a child subject. The parts are connected such as by wires or wireless communications.

FIG. 3C schematically illustrates an asthma-monitor 200 where part of which 200b is disposed on a subject and another part 200a disposed on a guardian or parent (representing any person, such as paramedic), according to exemplary embodiments of the invention. Parts 200a and 200b are linked or coupled or connected by linkage 402, such as wire or any other method such as wireless connection.

In some embodiments, asthma-monitor 200 is held on or attaches to a wrist or a finger by a thimble-like construction, or by a fastener such as elastic band, or buckle or hooks-and-loops or any appropriate fastener that is sufficient to acquire signals by the probes (or sensors) through the skin and to secure the device to the subject and/or guardian thereof.

Some potential or probable advantages and benefits of asthma-monitors as described above are:

Assessment or evaluation of asthma exacerbation during asthma attacks as they provide blood $CO_2$ (or close approximation thereof), contrary to alternative methods such as capnography which may be prone to lower accuracy due to arterial-alveolar gradient present during different pathological conditions.

They use a combination of $CO_2$ evaluation together with $O_2$ evaluation that provides an adequate clinical method to evaluate respiratory failure, as respiration involves an intricate balance between $O_2$, $CO_2$ and body metabolism.

They are small handy portable device wearable on a person.

They are inexpensive to produce as compared to other devices available for measuring $CO_2$, and can be offered at an affordable price to patients who need a respiratory monitor.

They allow asthma monitoring at home or trips outside and remote from medical facilities or during admission to a hospital or in first aid procedure.

They provide alerts that may be used to draw the attention of the subject (or guardian thereof) even during sleep.

They can be separated to a sensing part on a subject and control part on a guardian thereof.

They enable to report quantitative characteristics of the asthma conditions, such as while consulting with a physician over the telephone.

FIG. 4 illustrates a chart 500 of responses to $CO_2$ of capnograph 502c vs. a method of asthma-monitor for evaluation of blood $CO_2$ 502b according to exemplary embodiments of the invention. Vertical axis 504 represents $CO_2$ level (mmHg) and horizontal axis 506 represents breathing time (seconds). In a period of apnea between time indicated as 508s and 408e, the blood $CO_2$ 504b increases (insufficient breathing) while the capnograph readings 502c drops as the breathing and exhaling air flow is not sufficient, if at all, for the capnograph detection. The apnea simulates one of several respiratory conditions during which capnography measurements inherently deviate from the levels of arterial blood gases. On the other hand, the $CO_2$ measurement by the methods and apparatus described above ($CO_2$-Meter based on the principles of PCT/IL2009/000530) adequately agree with arterial blood $CO_2$.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A counter-implemented method for assessment of a respiratory condition of a subject, the method comprising:
    (a) acquiring from the subject a temporally varying hemodynamic waveform signal related to blood flow in a tissue of the subject, and generating a representative cycle indicative of blood flow during a cardiac cycle therefrom;
    (b) deriving from the representative cycle an evaluation of blood carbon dioxide ($CO_2$) of the subject by configuring a processing circuitry for:
        generating a derivative cycle by computing a time derivative of the representative cycle;
        determining key points and features in the derivative cycle; and
        determining a $CO_2$ level from the key points and features determined in the derivative cycle;
        wherein determining key points and features in the derivative cycle comprises determining a first point of maximum and determining a temporal distance between a first point and a second point;
    (c) acquiring from the subject at least one more signal relating to the respiratory or cardiovascular condition of the subject; and
    (d) determining the respiratory condition of the subject based on the blood $CO_2$, the at least one more signal and a relationship between the blood $CO_2$ and the at least one more signal.

2. The method according to claim 1, wherein the hemodynamic waveform signal is acquired during an exacerbation of an existing, previously known condition of the subject.

3. The method according to claim 2, wherein the existing, previously known condition of the subject comprises one or more of asthma, Chronic Obstructive Pulmonary Disease (COPD), cystic fibrosis, a chronic respiratory disease, metabolic derangement, a chronic cardiac condition and head trauma.

4. The method according to claim 2, wherein the existing, previously known condition of the subject comprises one or more of mechanical ventilation of the subject, supplemental oxygen intake by the subject, and medication use by the subject.

5. The method according to claim 1, wherein the respiratory condition comprises an asthma exacerbation and determining the respiratory condition comprises detecting and determining the asthma exacerbation.

6. The method according to claim 5, wherein determining the asthma exacerbation comprises comparing the blood $CO_2$ and the at least one more signal with obtained guidelines and values.

7. The method according to claim 6, wherein the obtained guidelines and values comprise at least one of Global Initiative for Asthma (GINA) and National Institutes of Health (NIH).

8. The method of claim 1, wherein determining a $CO_2$ level from the key points and features determined in the derivative cycle further comprises:
   determining a tangent to a slope following the first point of maximum;
   determining an intersection of the tangent with a time axis to obtain a third point; and
   computing an integral of an interval starting from the third point and having a length equivalent to the determined a temporal distance between a first point and a second point.

9. A device for evaluating a respiratory condition of a subject, the device comprising:
   (a) an implement disposable on the subject's skin comprising a processing circuitry, and structured to acquire a temporally varying hemodynamic waveform signal, generate therefrom a representative cycle indicative of blood flow during a cardiac cycle and derive from the representative cycle a blood $CO_2$ value of the subject or a close approximation thereof by configuring a processing circuitry for:
      generating a derivative cycle by computing a time derivative of the representative cycle;
      determining key points and features in the derivative cycle; and
      determining a $CO_2$ level from the key points and features determined in the derivative cycle;
      wherein determining key points and features in the derivative cycle comprises determining a first point of maximum and determining a temporal distance between a first point and a second point;
   (b) an oximeter disposable on the subject's skin and structured to provide an oxygen saturation value of the blood of the subject or a close approximation thereof; and
   (c) an apparatus structured to evaluate the respiratory condition of the subject based on the blood $CO_2$, oxygen saturation of the blood of the subject or close approximations thereof, and a relationship between the blood $CO_2$ and the oxygen saturation of the blood.

10. The device according to claim 9, wherein the respiratory condition comprises one or more of asthma, Chronic Obstructive Pulmonary Disease (COPD), cystic fibrosis, a chronic respiratory disease, metabolic derangement, a chronic cardiac condition and head trauma.

11. The device according to claim 9, wherein the apparatus is structured to evaluate the respiratory condition of the subject based on the blood $CO_2$ and oxygen saturation of the blood of the subject or close approximations thereof, and at least one of a provided respiration rate, heart rate, wheeze sound, pulsus paradoxus, or close approximations thereof.

12. The device according to claim 9, further comprising equipment providing one or more additional signals of the subject, or a close approximation thereof, and wherein the apparatus is further structured to evaluate the respiratory condition of the subject based also on the one or more additional signals.

13. The device according to claim 12, wherein the apparatus is structured to provide the respiration rate of the subject, or a close approximation thereof, from the temporally varying hemodynamic waveform signal.

14. The device according to claim 12, wherein the oximeter is structured to provide the heart rate of the subject, or a close approximation thereof.

15. The device according to claim 12, wherein the apparatus is structured to provide the heart rate of the subject, or a close approximation thereof, from a photoplethysmography signal provided by the oximeter.

16. The device according to claim 12, wherein the apparatus is structured to provide the heart rate of the subject, or a close approximation thereof, from the hemodynamic waveform signal.

17. The device according to claim 12, further comprising equipment to provide at least one of a respiration rate or heart rate of the subject, or close approximations thereof.

18. The device according to claim 12, further comprising equipment to provide a representation of wheeze sound of the subject, or a close approximation thereof.

19. The device according to claim 12, further comprising equipment to provide a representation of pulsus paradoxus of the subject, or a close approximation thereof.

20. The device according to claim 9, wherein the apparatus is structured to evaluate the respiratory condition of the subject by comparing the blood $CO_2$ and the oxygen saturation of the blood with provided guidelines and values.

21. The device according to claim 9, wherein the device comprises notification equipment for notifying the respiratory condition, and the apparatus is structured to provide a notification according to the respiratory condition.

22. The device of claim 9, wherein determining a $CO_2$ level from the key points and features determined in the derivative cycle further comprises:
   determining a tangent to a slope following the first point of maximum;
   determining an intersection of the tangent with a time axis to obtain a third point; and
   computing an integral of an interval starting from the third point and having a length equivalent to the determined a temporal distance between a first point and a second point.

* * * * *